United States Patent
DeCerce et al.

(10) Patent No.: US 12,303,290 B2
(45) Date of Patent: May 20, 2025

(54) MEDICAL SENSOR AND METHOD

(71) Applicant: HOWMEDICA OSTEONICS CORP., Mahwa, NJ (US)

(72) Inventors: Joseph DeCerce, Fort Lauderdale, FL (US); Wael Hazin, Plantation, FL (US)

(73) Assignee: HOWMEDICA OSTEONICS CORP., Mahwa, NJ (US)

( * ) Notice: Subject to any disclaimer, the term of this patent is extended or adjusted under 35 U.S.C. 154(b) by 182 days.

(21) Appl. No.: 17/158,126

(22) Filed: Jan. 26, 2021

(65) Prior Publication Data

US 2021/0228153 A1    Jul. 29, 2021

Related U.S. Application Data

(60) Provisional application No. 62/966,375, filed on Jan. 27, 2020.

(51) Int. Cl.
   *A61B 5/00*    (2006.01)
   *G01L 1/22*    (2006.01)

(52) U.S. Cl.
   CPC .......... *A61B 5/4851* (2013.01); *A61B 5/4528* (2013.01); *G01L 1/2262* (2013.01);
   (Continued)

(58) Field of Classification Search
   CPC .......... A61B 5/1036; A61B 2562/0247; A61B 2562/0261; A61B 2562/046;
   (Continued)

(56) References Cited

U.S. PATENT DOCUMENTS

| 5,311,880 A | 5/1994 | Lancaster et al. |
| 7,195,594 B2 | 3/2007 | Eigler et al. |

(Continued)

FOREIGN PATENT DOCUMENTS

| DE | 102010015890 A1 | 9/2011 | |
| WO | WO-2010092092 A1 * | 8/2010 | ............. G01L 1/148 |
| WO | WO 2019/009368 A1 | 1/2019 | |

OTHER PUBLICATIONS

WO-2010092092-A1 English translation (Year: 2010).*
International Preliminary Report on Patentability dated Jul. 28, 2022, in related application PCT/US2021/015077 (10 pages).

*Primary Examiner* — David J. McCrosky
(74) *Attorney, Agent, or Firm* — Bookoff McAndrews, PLLC

(57) ABSTRACT

A medical sensor is disclosed for mounting within a medical device. In one embodiment, more than one medical sensor is mounted to a printed circuit board using surface mount technology to accurately place the medical sensors in predetermined positions. The medical sensor is a sensor for measuring a force, pressure, or load. The medical sensor is manufactured in a process that supports consistency, matching, reliability, and performance. The medical sensor comprises a substrate, a dielectric layer overlying the substrate, and four strain gauges overlying the dielectric layer. Interconnect and pads are formed overlying the dielectric layer. The interconnect couples the four strain gauges into a full bridge Poisson gauge and couples the pads to the full bridge Poisson gauge. The active strain gauges are placed in a predetermined location on the substrate that support measurement of a force, pressure, or load applied to the substrate.

20 Claims, 12 Drawing Sheets

(52) U.S. Cl.
CPC ............... *A61B 2562/0247* (2013.01); *A61B 2562/0261* (2013.01); *A61B 2562/046* (2013.01)

(58) Field of Classification Search
CPC ... A61B 5/4851; A61B 5/4528; A61B 5/4839; A61B 5/4836; A61B 5/686; A61B 5/6878; G01G 3/1404; G01L 1/22; G01L 1/225; G01L 1/2287; G01L 5/162; G01L 5/161; G01L 1/2262; A61F 2/76
See application file for complete search history.

(56) References Cited

U.S. PATENT DOCUMENTS

| | | | |
|---|---|---|---|
| 7,381,910 B1 | 6/2008 | Wilkerson et al. | |
| 7,454,987 B2 | 11/2008 | Reger | |
| 7,483,731 B2 | 1/2009 | Haorau | |
| 7,699,770 B2 | 4/2010 | Hassler, Jr. et al. | |
| 7,862,513 B2 | 1/2011 | Eigler et al. | |
| 8,121,687 B2 | 2/2012 | Jensen et al. | |
| 8,157,789 B2 | 4/2012 | Leo et al. | |
| 8,298,227 B2 | 10/2012 | Leo et al. | |
| 8,316,719 B2 | 11/2012 | Majidi et al. | |
| 8,529,476 B2 | 9/2013 | Govari | |
| 8,740,879 B2 | 6/2014 | Martinson et al. | |
| 9,060,743 B2 | 6/2015 | Munro et al. | |
| 9,119,533 B2 | 9/2015 | Ghaffari | |
| 9,554,484 B2 | 1/2017 | Rogers et al. | |
| 9,841,331 B2 | 12/2017 | Wood et al. | |
| 9,993,921 B2 | 6/2018 | Lessing et al. | |
| 10,434,252 B2 | 10/2019 | Trombly et al. | |
| 10,820,862 B2 | 11/2020 | Rogers et al. | |
| 2002/0166385 A1* | 11/2002 | Bloom | B60R 21/01516 73/777 |
| 2006/0173366 A1 | 8/2006 | Hasegawa | |
| 2007/0000335 A1* | 1/2007 | Morimoto | G01L 5/1627 73/862.045 |
| 2007/0287879 A1* | 12/2007 | Gelbart | A61B 17/12022 600/16 |
| 2011/0152725 A1* | 6/2011 | Demir | A61B 5/103 600/587 |
| 2013/0204157 A1 | 8/2013 | Clark et al. | |
| 2014/0288464 A1* | 9/2014 | Stein | A61F 2/4657 600/595 |
| 2015/0250420 A1 | 9/2015 | Longinotti-Buitoni et al. | |
| 2015/0320472 A1 | 11/2015 | Ghaffari | |
| 2017/0030784 A1* | 2/2017 | Mason | G01L 5/0047 |
| 2017/0123548 A1* | 5/2017 | Shih | G01L 1/22 |
| 2017/0176167 A1* | 6/2017 | Keller | G01L 1/225 |
| 2017/0312481 A1 | 11/2017 | Covington et al. | |
| 2018/0085061 A1 | 3/2018 | Heisig et al. | |
| 2018/0103899 A1* | 4/2018 | Cahan | G01L 5/1627 |
| 2018/0360534 A1 | 12/2018 | Teplitsky et al. | |
| 2019/0091098 A1 | 3/2019 | Butler et al. | |
| 2020/0129261 A1* | 4/2020 | Eschbach | A61B 90/06 |

\* cited by examiner

MEDICAL SENSOR AND METHOD

FIELD

The present invention pertains generally to medical devices, and particularly to, but not exclusively to, a medical sensor for generating sensor data.

BACKGROUND

The skeletal system of a mammal is subject to variations among species. Further changes can occur due to environmental factors, degradation through use, and aging. An orthopedic joint of the skeletal system typically comprises two or more bones that move in relation to one another. Movement is enabled by muscle tissue and tendons attached to the skeletal system of the joint. Ligaments hold and stabilize the one or more joint bones positionally. Cartilage is a wear surface that prevents bone-to-bone contact, distributes load, and lowers friction.

There has been substantial growth in the repair of the human skeletal system. In general, orthopedic joints have evolved using information from simulations, mechanical prototypes, and patient data that is collected and used to initiate improved designs. Similarly, the tools being used for orthopedic surgery have been refined over the years but have not changed substantially. Thus, the basic procedure for repair of the musculoskeletal system has been standardized to meet the general needs of a wide distribution of the population. Although the tools, procedure, and artificial joints meet a general need, each procedure is subject to significant variation from patient to patient. The correction of these individual variations relies on the skill of the surgeon to adapt and fit the replacement joint using the available tools to the specific circumstance. It would be of benefit if quantitative measurement data is incorporated with the subjective skills of the surgeon.

BRIEF DESCRIPTION OF THE DRAWINGS

Various features of the system are set forth with particularity in the appended claims. The embodiments herein, can be understood by reference to the following description, taken in conjunction with the accompanying drawings, in which:

DETAILED DESCRIPTION

Figure 1:
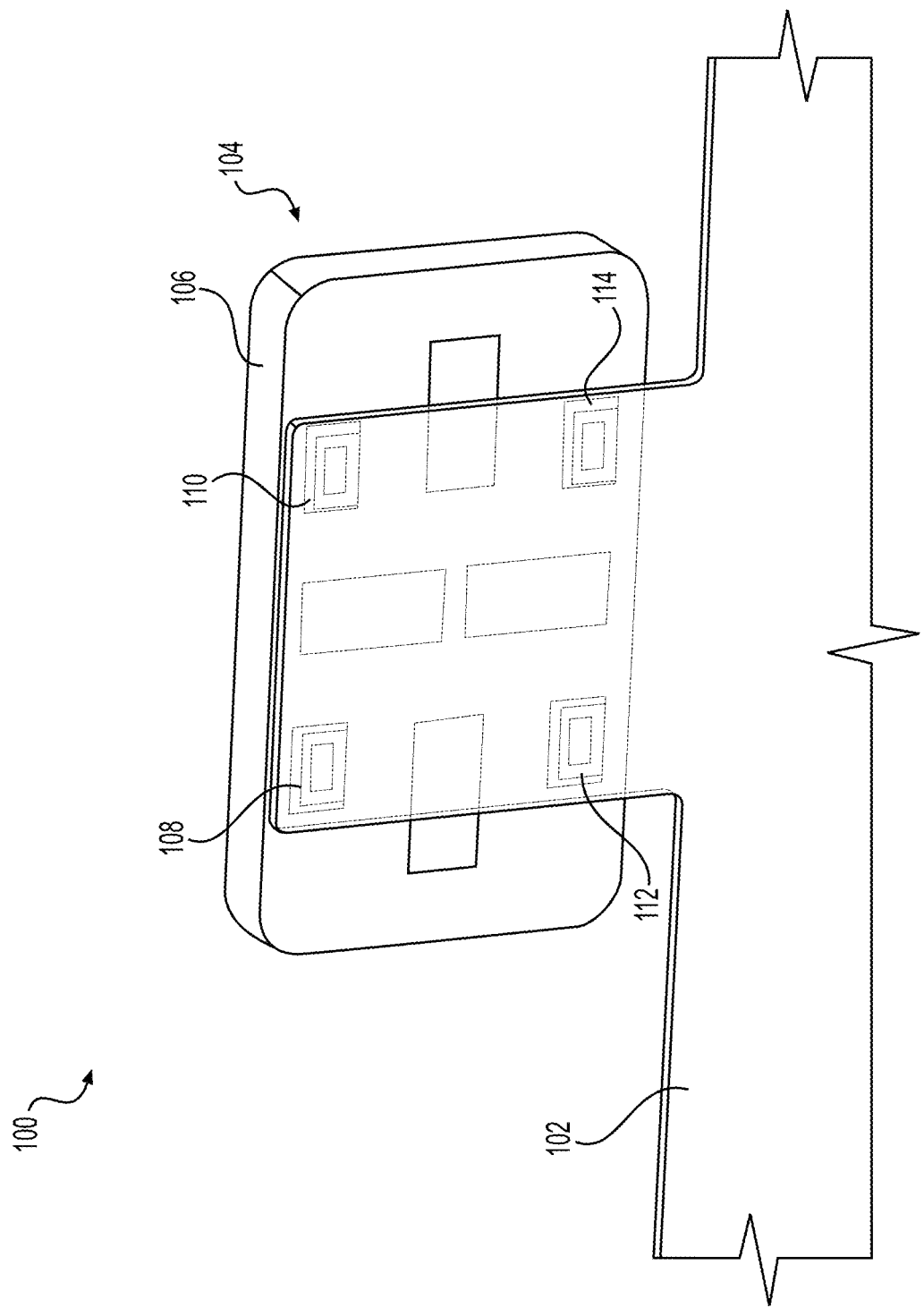
FIG. 1 is an illustration of a portion of a medical device in accordance with an example embodiment.

The following description of exemplary embodiment(s) is merely illustrative in nature and is in no way intended to limit the invention, its application, or uses.

Processes, techniques, apparatus, and materials as known by one of ordinary skill in the art may not be discussed in detail but are intended to be part of the enabling description where appropriate.

While the specification concludes with claims defining the features of the invention that are regarded as novel, it is believed that the invention will be better understood from a consideration of the following description in conjunction with the drawing figures, in which like reference numerals are carried forward.

The example embodiments shown herein below of the device are illustrative only and do not limit use for other parts of a body or for other applications. The device is used to measure at least parameter to generate quantitative measurement data. The device can be used on the knee, hip, ankle, spine, shoulder, hand, wrist, foot, fingers, toes, bone, muscle, ligaments tendon and other areas of the musculoskeletal system. In general, the principles disclosed herein are meant to be adapted for use in other locations of the musculoskeletal system. The following description of embodiment(s) is merely illustrative in nature and is in no way intended to limit the invention, its application, or uses.

For simplicity and clarity of the illustration(s), elements in the figures are not necessarily to scale, are only schematic and are non-limiting, and the same reference numbers in different figures denote the same elements, unless stated otherwise. Additionally, descriptions and details of well-known steps and elements are omitted for simplicity of the description. Notice that once an item is defined in one figure, it may not be discussed or further defined in the following figures.

The terms "first", "second", "third" and the like in the Claims or/and in the Detailed Description are used for distinguishing between similar elements and not necessarily for describing a sequence, either temporally, spatially, in ranking or in any other manner. It is to be understood that the terms so used are interchangeable under appropriate circumstances and that the embodiments described herein are capable of operation in other sequences than described or illustrated herein.

Processes, techniques, apparatus, and materials as known by one of ordinary skill in the art may not be discussed in detail but are intended to be part of the enabling description where appropriate.

The orientation of the x, y, and z-axes of rectangular Cartesian coordinates is assumed to be such that the x and y axes define a plane at a given location, and the z-axis is normal to the x-y plane. The axes of rotations about the Cartesian axes of the device are defined as yaw, pitch and roll. With the orientation of the Cartesian coordinates defined in this paragraph, the yaw axis of rotation is the z-axis through body of the device. Pitch changes the orientation of a longitudinal axis of the device. Roll is rotation about the longitudinal axis of the device. The orientation of the X, Y, Z axes of rectangular Cartesian coordinates is selected to facilitate graphical display on computer screens having the orientation that the user will be able to relate to most easily. Therefore the image of the device moves upward on the computer display whenever the device itself moves upward for example away from the surface of the earth. The same applies to movements to the left or right.

Although inertial sensors are provided as enabling examples in the description of embodiments, any tracking device (e.g., a GPS chip, acoustical ranging devices, an accelerometer, a magnetometer, a gyroscope, an inclinometers, and MEMs devices) can be used within the scope of the embodiments described.

At least one embodiment is directed to a kinetic orthopedic measurement system to aid a surgeon in determining real time alignment, range of motion, loading, impingement, and contact point of orthopedic implants. Although the system is generic to any orthopedic surgery (e.g., spinal, shoulder, knee, hip, ankle, wrist, finger, toe, bone, musculoskeletal, etc.) the following examples deal with orthopedic surgery as a non-limiting example of an embodiment of the invention.

The non-limiting embodiment described herein is related to quantitative measurement based orthopedic surgery and referred to herein as the kinetic system. The kinetic system includes a sensor system that provides quantitative measurement data and feedback that can be provided visually, audibly, or haptically to a surgeon or surgical team. The kinetic system provides the surgeon real-time dynamic data regarding force, pressure, or loading on the joint, bone, or musculoskeletal system, contact and congruency through a full range of motion, and information regarding impingement.

In general, kinetics is the study of the effect of forces upon the motion of a body or system of bodies. Disclosed herein is a system for kinetic assessment of the musculoskeletal system. The kinetic system can be for the installation of prosthetic components or for monitoring and assessment of permanently installed components to the musculoskeletal system. For example, installation of a prosthetic component can require one or more bone surfaces to be prepared to receive a device or component. The kinetic system is designed to take quantitative measurements of at least the load, position of load, or alignment with the forces being applied to the joint similar to that of a final joint installation. The sensored measurement components are designed to allow ligaments, tissue, and bone to be in place while the quantitative measurement data is taken. This is significant because the bone cuts take into account the kinetic forces where a kinematic assessment and subsequent bone cuts could be substantial changed from an alignment, load, and position of load once the joint is reassembled.

A prosthetic joint installation can benefit from quantitative measurement data in conjunction with subjective feedback of the prosthetic joint to the surgeon. The quantitative measurements can be used to determine adjustments to bone, prosthetic components, or tissue prior to final installation. Permanent sensors can also be housed in final prosthetic components to provide periodic data related to the status of the implant. Data collected intra-operatively and long term can be used to determine parameter ranges for surgical installation and to improve future prosthetic components. One or more sensors used post-operatively can be used to monitor motion of the musculoskeletal system to determine how the repair is performing and provide feedback based on quantitative measurement data. The physical parameter or parameters of interest can include, but are not limited to, measurement of alignment, load, force, pressure, position, displacement, density, viscosity, pH, spurious accelerations, color, movement, chemical composition, particulate matter, structural integrity, and localized temperature. Often, several measured parameters are used to make a quantitative assessment. A graphical user interface can support assimilation of measurement data. Parameters can be evaluated relative to orientation, alignment, direction, displacement, or position as well as movement, rotation, or acceleration along an axis or combination of axes by wireless sensing modules or devices positioned on or within a body, instrument, appliance, vehicle, equipment, or other physical system.

At least one embodiment is directed to a system for trialing or permanently installing a prosthetic joint within the musculoskeletal system for stability, alignment, balance, and range of motion using quantitative measurement data. Monitoring the prosthetic joint with one or more sensors can be used for measuring parameters related to rehabilitation, infection, pain, reliability, performance, or wear. The prosthetic joint has at least one prosthetic component having an articular surface configured to support movement of the prosthetic joint. In one embodiment, the prosthetic component will have a plurality of strain gauge sensors underlying the articular surface and a position measurement system. The prosthetic component is configured to measure position, load magnitude, position of applied load, slope, rotation, range of motion, or movement. In one embodiment, a remote system is configured to wirelessly receive quantitative measurement data from the sensored prosthesis such that the remote system is configured to display parameters measured by the one or more sensors.

Embodiments of the invention are broadly directed to measurement of physical parameters. Many physical parameters of interest within physical systems or bodies can be measured by evaluating changes in resistance as a structure is under strain. As one example, a strain gauge can be placed on a structure that is under a variable load. The structure deforms under the load thereby changing the resistance of the strain gauge as it deforms with the structure. The physical parameter or parameters of interest can include, but are not limited to, measurement of load, force, pressure, displacement, density, viscosity, localized temperature. These parameters can be evaluated by measuring changes in the resistance of a strain gauge relative to orientation, alignment, direction, or position as well as movement, rotation, or acceleration along an axis or combination of axes by wireless sensing modules or devices positioned on or within a body, instrument, appliance, vehicle, equipment, or other physical system.

In all of the examples illustrated and discussed herein, any specific materials, temperatures, times, energies etc. . . . for process steps or specific structure implementations should be interpreted to be illustrative only and non-limiting. Processes, techniques, apparatus, and materials as known by one of ordinary skill in the art may not be discussed in detail but are intended to be part of an enabling description where appropriate.

Note that similar reference numerals and letters refer to similar items in the following figures. In some cases, numbers from prior illustrations will not be placed on subsequent figures for purposes of clarity. In general, it should be assumed that structures not identified in a figure are the same as previous prior figures.

In the present invention these parameters are measured with an integrated wireless sensing module or device comprising an i) encapsulating structure that supports sensors and contacting surfaces and ii) an electronic assemblage that integrates a power supply, one or more sensors, one or more strain gauges, transducers, one or more inertial sensors, antennas and electronic circuitry that processes measurement data as well as controls all operations of energy conversion, propagation, and detection and wireless communications. The wireless sensing module or device can be positioned on or within, or engaged with, or attached or affixed to or within, a wide range of physical systems including, but not limited to instruments, appliances, vehicles, equipments, or other physical systems as well as animal and human bodies, for sensing and communicating parameters of interest in real time.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the invention.

In the example of a prosthetic joint can be optimized using quantitative measurement data from one or more sensors. The patient can be monitored after being released from surgery and during rehabilitation using sensor technology. The measurement data can support optimization of therapy and indicate problems that may occur. The effects of the therapy program using the intelligent prosthetic components can be linked to proper joint function and the patient can be educated on their recovery relative to their specific plan and compared with data from other patients. In one embodiment, when the prosthesis is activated, the data will be transmitted (RF/Bluetooth) to a patient recovery application. In one embodiment, the application can be on a computer or a device such as a smart phone. The quantitative measurement data from the sensors will be uploaded into a cloud based VPN (virtual private network) that is HIPPA Compliant. The quantitative measurement data can be assessed by one or more computer programs and updates, work flows, and the measurement data can be sent to the treating physician and health care team. The intelligent prosthesis can be used to support post-op exercises, treatment, or pharmaceuticals that can accelerate the healing phase. Furthermore, different reconstruction techniques can be compared with real-time data. Evaluations of the effects of reconstruction when combined with multi ligamentous injuries can also be analyzed. Healing phase monitoring related to graft adherence to the host tunnels (bone to bone, tendon to bone, composite to bone) can provide quantitative measurement data related thereto. Other important parameters can also be generated such as improving ROM and terminal extension, achieving improved muscle strength, improved proprioception, improved stability, and improved gait mechanics.

FIG. 1 is an illustration of a portion of a medical device 100 in accordance with an example embodiment. In general, medical device 100 includes one or more sensors, electronic circuitry, and a power source. Medical device 100 is configured to measure one or more parameters, control a measurement process, and transmit measurement data. More specifically, medical device 100 is designed for manufacturability where sensors and electronic components can be coupled to a printed circuit board 102 using surface mount technology or similar processes. The printed circuit board 102 can then be placed in a housing whereby the sensors align to the housing at predetermined locations to support measurement of the one or more parameters. Implementing an automated process improves performance, reduces variability, lower cost, and increases reliability of medical device 100.

In one embodiment, medical device 100 is configured to measure a force, pressure or load applied to a housing. Sensor 104 is configured as a surface mount device that can be picked up, placed, and coupled to a printed circuit board 102 in an automated process. In the example, sensor 104 comprises a plurality of strain gauge sensors formed simultaneously as an integrated device. Forming the strain gauges simultaneously on sensor 104 allows each strain gauge to match each other to have equal or substantially equal performance characteristics. Pads 108, 110, 112, and 114 are patterned and formed on a layer of sensor 104 to couple to corresponding pads on printed circuit board 102. In the example, pads 108, 110, 112, and 114 are soldered to corresponding pads on printed circuit board 102. Electrical interconnect is also formed on the layer of sensor 104 that couple to pads 108, 110, 112, and 114 and the plurality of strain gauges. Printed circuit board 102 can be a flexible printed circuit board or a rigid printed circuit board. Printed circuit board 102 can include one or more layers of interconnect configured to couple electronic components and sensors together to form a circuit.

Figure 2:
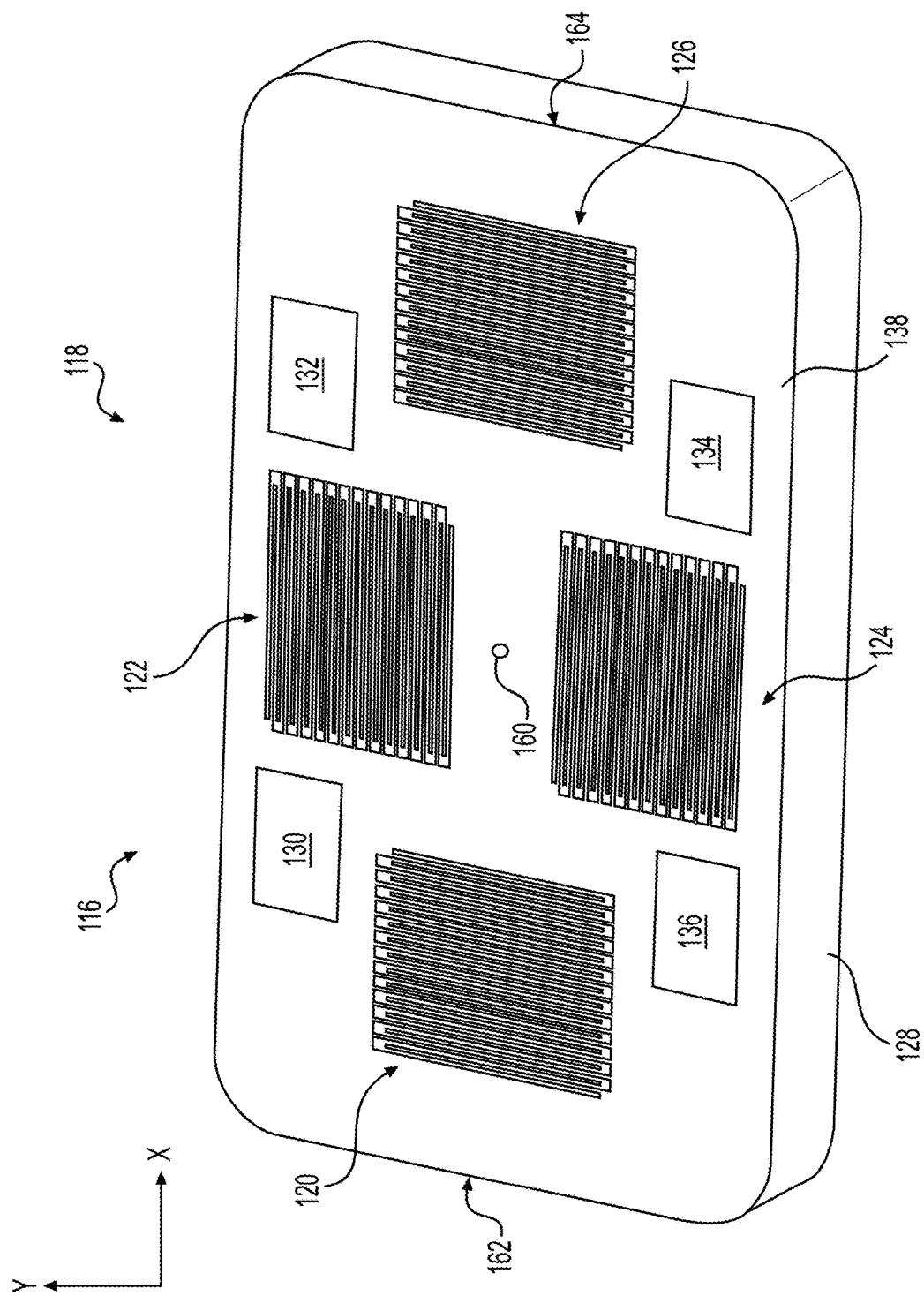
FIG. 2 is an illustration of a medical sensor for surface mounting in a medical device in accordance with an example embodiment.

FIG. 2 is an illustration of a medical sensor 116 for surface mounting in a medical device in accordance with an example embodiment. Medical sensor 116 is configured to measure a force, pressure, or load. Medical sensor 116 comprises a substrate 128, a strain gauge 120, a strain gauge 122, a strain gauge 124, and a strain gauge 126. In one embodiment, a dielectric layer 138 overlies substrate 128. Strain gauges 120, 122, 124, and 126 overlie dielectric layer 138 and form a sensor array 118. In one embodiment, strain gauges 120, 122, 124, and 126 are formed simultaneously using photolithography to pattern and etch each device at the same time for superior device to device matching. Interconnect and pads 130, 132, 134, and 136 are formed overlying dielectric layer 138. The interconnect is patterned to couple strain gauges 120, 122, 124, and 126 into a full bridge Poisson gauge. The interconnect further couples inputs and outputs of the full bridge Poisson gauge to pads 130, 132, 134, and 136 for surface mounting to a printed circuit board.

In one embodiment, a strain gauge comprises a resistive element. The resistive element is designed to conform to a substrate. The substrate is selected to elastically deform when a force, pressure, or load is applied. The strain gauge is coupled to the substrate such that the strain gauge is put under strain when the substrate elastically deforms. The deformation of the substrate applies a tensile or compressive strain such that the length or width of the resistive element is modified thereby resulting in a corresponding change in the resistance of the strain gauge. For example, the substrate is selected to elastically deform over an applied predetermined range of force, pressure, or load. The strain gauge is designed to provide a measurable resistance change over the applied predetermined range of force, pressure, or load. In one embodiment, the change in resistance is converted to a voltage. In one embodiment, the strain gauge can be used in a prosthetic component to measure loading in a range of 20 lbs. to 150 lbs. Ideally, the strain gauge operates linearly over the predetermined range of force, pressure, or load. Alternatively, the strain gauge can calibrated to reduce non-linearities over the predetermined loading range to provide accurate measurement.

In general, substrate 128 of medical sensor 116 is configured to elastically deform along the X-axis with little deformation along the Y-axis. The X and Y axis are shown on FIG. 2 and relate to a plane of the surface of substrate 128. As illustrated strain gauges 122 and 124 are the active devices used to measure a resistance change when a force, pressure, or load is applied to substrate 128. In other words, a force, pressure, or load applied to medical sensor 116 bends or deforms substrate 128 along the X-axis. The resistance of strain gauges 122 and 124 corresponds to the deformation of substrate 128. The resistive element of the strain gauge is made to have substantial length in a first direction and a short length in a second direction. The substantial length of the resistive element is designed into the first direction to be responsive to the force, pressure, or load in changing the resistance. Conversely, the short length of the resistive element is designed to produce little change in the resistance in the second direction. Strain gauge 122 and strain gauge 124 are shown having substantial length along the X-axis while having a short length along the Y-axis. In one embodiment, the length of strain gauges 122 and 124 along the X-axis is increased by having multiple interconnected rows of the resistive element in series. This allows strain gauges 122 and 124 to have considerable length along the X-axis while having a compact shape that can fit within a predetermined area. Furthermore, the width of the resistive material used for strain gauges 122 and 124 are increased in the small lengths in the Y-axis direction to minimize resistance changes due to deformation. The increased width of strain gauges 122 and 124 along the Y-axis greatly reduces the resistance of strain gauge 122 and strain gauge 124 in the Y-axis direction thereby decreasing the sensitivity of measurement in the direction of the Y-axis. Thus, strain gauges 122 and 124 are designed to be sensitive in the X-axis direction while having reduced sensitivity in the Y-axis direction. In one embodiment, strain gauges 122 and 124 are placed in an area of substrate maximum deformation of medical sensor 116.

Strain gauges 120, 122, 124, and 126 are placed in a full bridge Poisson gauge configuration. Strain gauges 120 and 126 are non-active in the full bridge Poisson gauge configuration as they are oriented to measure deformation in the direction of the Y-axis. The full bridge Poisson gauge configuration will be discussed in more detail in FIG. 3. In one embodiment, strain gauges 120, 122, 124, and 126 are formed identical to one another. The orientation of strain gauges 120 and 126 are placed on substrate 128 having a substantial length along the Y-axis and a minimal length along the X-axis. In one embodiment, strain gauges 120 and 126 are placed at locations where low deformation or low strain occurs. In one embodiment, the length of strain gauges 120 and 126 along the Y-axis is increased by having multiple interconnected rows of the resistive element in series. This allows strain gauges 120 and 126 to have considerable length along the Y-axis while having a compact shape that can fit within a predetermined area. The width of the resistive material used for strain gauges 120 and 126 are increased in the small lengths in the direction of the X-axis. The increased width of strain gauges 120 and 126 in the direction of the X-axis greatly reduces the resistance or change in resistance due to deformation of substrate 128. In one embodiment, strain gauges 120 and 126 are identical to strain gauges 122 and 124 except for orientation to the X and Y-axis and location on substrate 128. Thus, strain gauges 122 and 124 are sensitive to deformation of substrate 128 in the direction of the Y-axis while having reduced sensitivity to deformation of substrate 128 in the direction of the X-axis. In one embodiment, strain gauges 120, 122, 124, and 126 can be premade strain gauges that are coupled by an adhesive to substrate 128.

Figure 3:
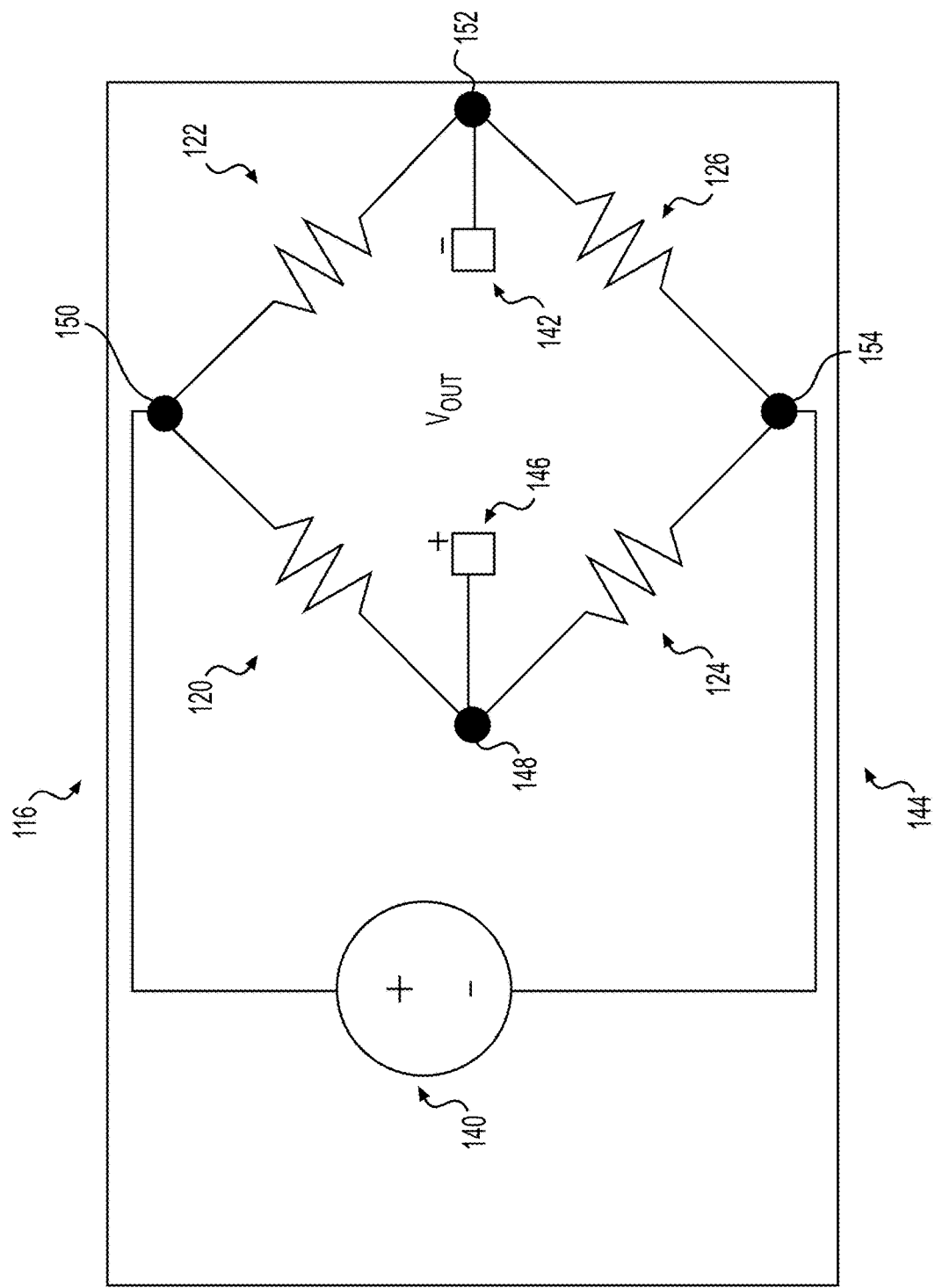
FIG. 3 is an illustration of the configuration of the medical sensor in accordance with an example embodiment.

FIG. 3 is an illustration of the configuration of medical sensor 116 in accordance with an example embodiment. Components of FIG. 2 will be referred to in the explanation of a full bridge Poisson gauge 144 configuration. In one embodiment, strain gauges 120, 122, 124, and 126 are coupled together to form full bridge Poisson gauge 144. Strain gauge 120 has a first terminal coupled to node 148 and a second terminal coupled to node 150. Strain gauge 122 has a first terminal coupled to node 150 and a second terminal coupled to node 152. Strain gauge 126 has a first terminal coupled to node 152 and a second terminal coupled to node 154. Strain gauge 124 has a first terminal coupled to node 154 and a second terminal coupled to node 148.

In one embodiment, a voltage source 140 is coupled to full bridge Poisson gauge 144 to bias the circuit when used in medical sensor 116. Voltage source 140 has a positive terminal coupled to node 150 and a negative terminal coupled to node 154. A voltage output of the full bridge Poisson gauge 144 is provided at an output 146 and an output 142. In one embodiment, output 146 and output 142 respectively correspond to a positive output and a negative output of the full bridge Poisson gauge 144. In one embodiment, the positive terminal and the negative terminal of voltage source 140 couples respectively to pad 130 and pad 136 of medical sensor 116. Pad 130 and pad 136 respectively correspond to node 150 and node 154 of the full bridge Poisson gauge 144. In one embodiment, output 146 and output 142 of the full bridge Poisson gauge 144 couples respectively to pad 132 and pad 134. Pad 132 and pad 134 respectively corresponds to node 148 and node 152 of full bridge Poisson gauge 144. Thus, a voltage can be provided to pads 130 and 136 to bias full bridge Poisson gauge 144 and the output voltage measured across pads 132 and 134. The output voltage measured across pads 132 and 134 corresponds to the force, pressure, or load applied to medical sensor 116.

Placing a plurality of resistors in a bridge configuration as shown in FIG. 3 has been found to accurately measure unknown resistance. The bridge configuration also has been used to measure small changes in resistance. Strain gauges 120, 122, 124, and 126 are variable resistors. In one embodiment, strain gauges 120, 122, 124, and 126 are formed identically having the same resistance on substrate 128. The only difference between strain gauges 120, 122, 124, and 126 are the location on substrate 128 and the orientation of each strain gauge. Strain gauges 120, 122, 124, and 126 couple to substrate 128 such that a force, pressure, or load applied to substrate 128 places a strain on one or more of the strain gauges that will change a resistance value that corresponds to the force, pressure, or load. The bridge configuration supports improved sensitivity, reduced noise, measurement stability, linearity of measurement, and reduced hysteresis. Medical sensor 116 is configured in a unique manner to support accurate, repeatable, and cost efficient force, pressure, or load sensing for medical applications. In one embodiment, medical sensor 116 is configured for being used in an automated process for building a prosthetic component that can measure loading applied by a musculoskeletal system. In one embodiment, a plurality of medical sensors 116 are used to measure loading applied by a musculoskeletal system to determine load magnitude of the applied load and position of applied load.

Referring briefly to FIG. 2, substrate 128 is rectangular in shape. The X-axis is parallel to a long side of substrate 128. The Y-axis is parallel to a short side of substrate 128. Substrate 128 has a center point 160. In one embodiment, medical sensor 116 is configured to measure a force, pressure, or load applied to center point 160. The force, pressure, or load applied to substrate 128 can comprise an area larger than depicted by center point 160 but the force, pressure, or load is directed to an area centered to or around center point 160. In one embodiment, an origin of the X-axis and the Y-axis corresponds to center point 160. Strain gauges 122 and 124 are the active devices of medical sensor 116. Strain gauge 122 is above the X-axis but centered on the Y-axis. Strain gauge 124 is below the X-axis but centered on the Y-axis. Note that strain gauge 122 and strain gauge 124 are configured to measure strain or deformation of substrate 128 along or parallel to the X-axis.

In one embodiment, strain gauges 120 and 126 are non-active devices of medical sensor 116. Strain gauge 120 is placed to the left of the Y-axis and strain gauge 126 is placed to the right of the Y-axis. In one embodiment, strain gauges 122 and 124 are placed physically closer to center point 160 than strain gauges 120 and 126. Note that the strain gauges 120 and 126 are at least a distance of one half of the length or more of strain gauges 122 or 124 from center point 160. Strain gauges 120 126 are aligned to measure strain or deformation the direction of the Y-axis.

As mentioned previously, strain gauges 122 and 124 are the active devices configured for measuring deformation or strain when a force, pressure, or load is applied to substrate 116. In one embodiment, substrate 128 couples to a medical device such that a first end 162 and a second end 164 of substrate 128 of medical sensor 116 are supported. Applying a force, pressure, or load to an area around center point 160 will place substrate 128 under strain. Substrate 128 will elastically deform in the direction of the X-axis thereby changing the electrical resistance of strain gauges 122 and 124. The elastic deformation of substrate 128 will deform strain gauges 122 and 124 in a manner that results in a change in resistance. Strain gauges 122 and 124 comprise resistive links in series to form a long resistive path in the direction of the X-axis. The resistive links are placed at or near center point 160 where a maximum deformation occurs. Thus, the sensitivity to change is increased in strain gauges 122 and 124 since the deformation will affect most or all the resistive links of each device. As shown, strain gauge 122 couples between node 150 and node 152 of full bridge Poisson gauge 144. Node 150 couples to a positive terminal of voltage source 140. Node 152 corresponds to output 142. Strain gauge 124 couples between node 148 and node 154. Node 154 couples to the node to a negative terminal of voltage source 140. Node 148 couples to output 146. As mentioned previously strain gauges 120 and 126 are non-active devices. Placing strain gauges 120 and 126 respectively near first end 162 and second end 164 of medical device 116 minimizes deformation applied to the devices. Moreover, the deformation occurs in the direction of the X-axis and strain gauges 120 and 126 are oriented to measure deformation or strain in the direction of the Y-axis. Thus, the resistance of strain gauges 120 and 126 should change little under deformation of substrate 128.

In one embodiment, the resistance of strain gauges 120, 122, 124, and 126 are greater than 10,000 ohms. The high resistance of strain gauges 120, 122, 124, and 126 supports battery operation in a surgical environment where the time of use of medical device 116 can vary significantly. The resistance change in strain gauges 122 and 124 generates an output voltage across outputs 146 and 142 based on the force, pressure, or load applied to substrate 128. For example, if strain gauges 120, 122, 124, and 126 have identical resistances the voltage at output 142 and output 146 would be the same. Thus, the voltage measured across outputs 142 and 146 would be zero corresponding to a quiescent condition where no force, pressure, or load is applied to substrate 128. In one embodiment, applying a force, pressure, or load to substrate 128 increases a resistance of strain gauges 122 and 124. Assuming that strain gauges 122 and 124 are affected by the force, pressure, or load applied to substrate 128 equally due to the force, pressure, or load application at the center of substrate 128 and the symmetry of placement of strain gauges 120, the change in resistance of strain gauges 122 and 124 would be substantially equal. Alternatively, the force, pressure, or load can applied across the entire width of substrate 128 in the direction of the Y-axis for a predetermined distance along the X-axis symmetrical about center point 160.

Note that the placement of strain gauge 122 couples to the positive terminal of voltage source 140 while strain gauge 124 couples to the negative terminal of the voltage source 140. The divider network of full bridge Poisson gauge 144 is such that the changes in resistance of the active devices results in an additive measurable output voltage. A change in resistance of strain gauge 122 produces a corresponding change at output 142. A change in resistance of strain gauge 124 produces a corresponding opposite change in voltage at output 148. For example, an increase in resistance of strain gauges 122 and 124 will result in a reduction in voltage at output 142 and an increase in voltage at output 146 thereby resulting in a net voltage increase across outputs 146 and 142. The increase across outputs 146 and 142 is twice the absolute voltage magnitude change across either strain gauge 122 or strain gauge 124 thereby increasing the sensitivity of measurement. Conversely, a decrease in resistance of strain gauges 122 and 124 will result in an increase in voltage at output 142 and a decrease in voltage at output 146 thereby resulting in a voltage decrease across outputs 146 and 142. The decrease across outputs 146 and 142 is twice the absolute voltage magnitude change across either strain gauge 122 or strain gauge 124. In one embodiment, the voltage output can be linear over the force, pressure, or load range. Alternatively, medical sensor 116 can be calibrated to remove non-linearities to measure accurately across the force, pressure, of load range.

Figure 4:
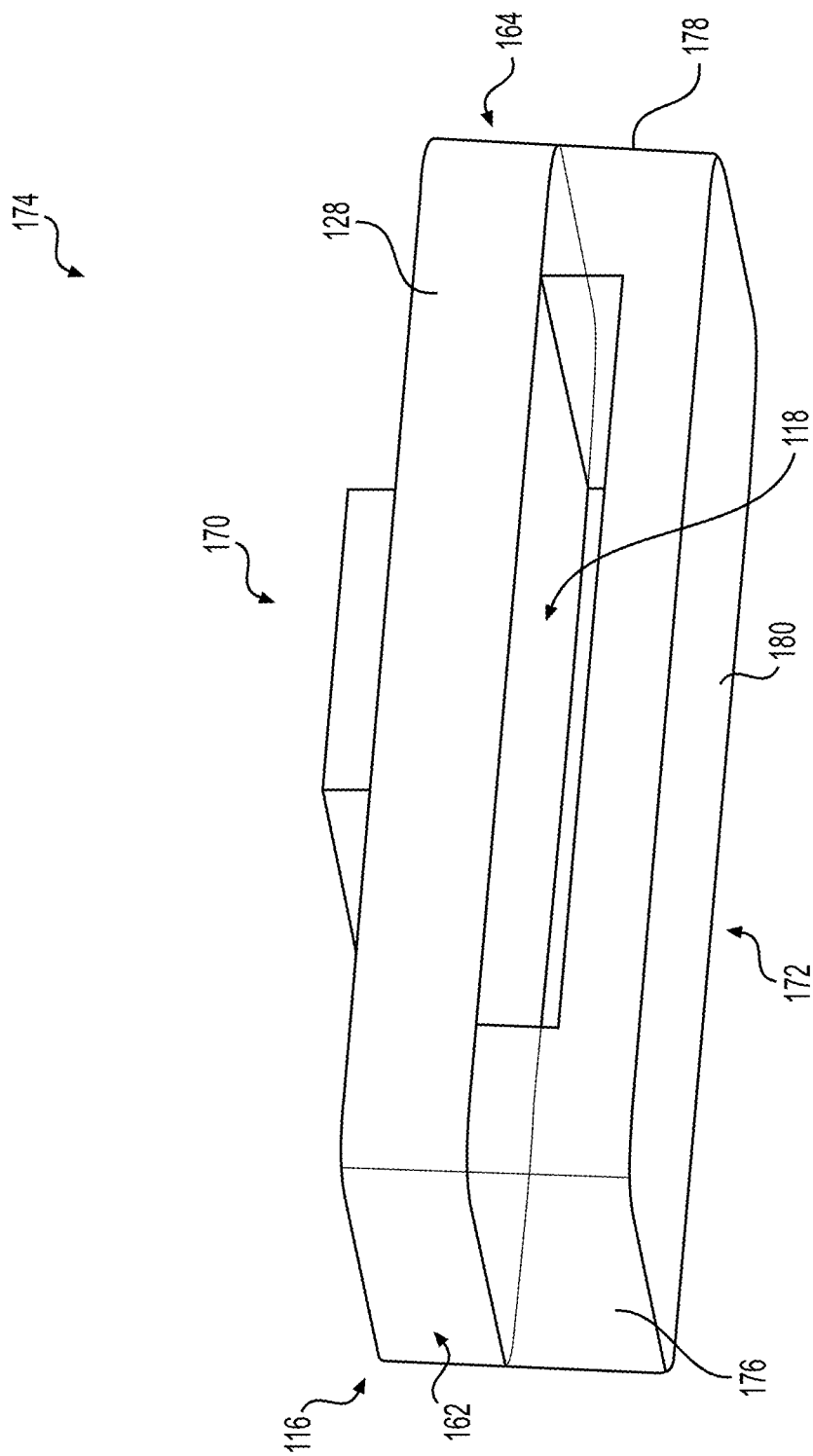
FIG. 4 is an illustration of the medical sensor coupled to a portion of a medical device in accordance with an example embodiment.

FIG. 4 is an illustration of medical sensor 116 coupled to a portion of a medical device 174 in accordance with an example embodiment. A force, pressure, or load is applied to structure 170 of medical device 174. In discussing medical device 174 the components of medical sensor 116 will be referred to as disclosed in FIG. 2. Structure 170 couples to an area around center point 160 of substrate 128 of medical sensor 116. In one embodiment, structure 170 is rectangular in shape and couples to an area of substrate 128 that corresponds to a location of strain gauges 122 and 124. In one embodiment, structure 170 is placed on a side opposite from where strain gauges 122 and 124 reside such that structure 170 overlies strain gauges 122 and 124. In one embodiment, structure 170 of medical device 170 couples to a first side of medical sensor 116 and strain gauges 120, 122, 124, and 126 couple to a second side of medical sensor 116.

A structure 172 of medical device 174 couples to the second side of medical sensor 116. As mentioned previously, the second side of medical sensor 116 includes strain gauges 120, 122, 124, and 126. Structure 172 comprises a substrate 180, a support 176, and a support 178. Supports 176 and 178 couple respectively to a first end 162 of medical sensor 116 and a second end 164 of medical sensor 116. Supports 176 and 178 suspend medical sensor 116 above substrate 180 of medical device 174. A force, pressure, or load applied to structure 170 of medical device 174 deforms substrate 128 of medical sensor 116 in a manner that creates strain in the direction of the X-axis and almost no strain in the direction of Y-axis. The force, pressure, or load applied to structure 170 causes substrate 128 to bow or deform towards substrate 180. The deformation produces a resistance change in strain gauges 122 and 124 that is configured to be converted to a voltage measured by electronic circuitry within medical device 174. The voltage output by medical sensor 116 corresponds to the force, pressure, or load applied to structure 170 of medical device 174. In one embodiment, the voltage output by medical sensor 116 in a quiescent state where structure 170 is unloaded will be zero volts.

In one embodiment, structure 170 distributes a force, pressure, or load to the first side of medical sensor 116 across an entire width (in the direction of the Y-axis) of substrate 128. Structure 170 is configured to distribute the force, pressure, or load approximately equal over the surface area of structure 170 coupling to substrate 128 of medical sensor 116. Applying the force, pressure, or load in this manner minimizes any strain on substrate 128 in the direction of the Y-axis but maximizes strain on substrate 128 in the direction of the X-axis. Supports 176 and 178 respectively couple to first end 162 and second end 164 of substrate 128 on the second side across the entire width (in the direction of the Y-axis) of substrate 128. Furthermore, strain gauges 120 and 126 reside outside regions of maximum strain on substrate 128 such that strain gauges 120 and 126 do not underlie structure 170 of medical device 174. Strain gauges 120 and 126 are non-active because medical sensor 116 is configured to produce no strain on substrate 128 of medical sensor 116 in the direction of Y-axis when a force, pressure, or load is applied to structure 170 of medical device 174. Thus, the resistance of strain gauges 120 and 126 is configured not to change (or change very little) during a measurement of medical sensor 116 in the full bridge Poisson gauge 144 configuration.

Figure 5:
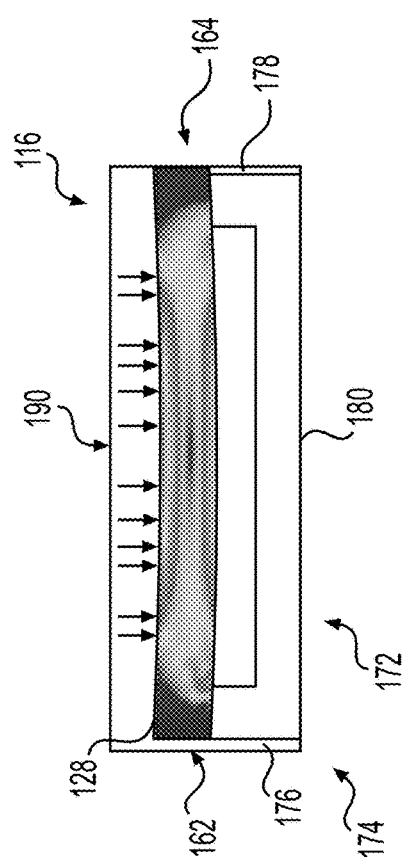
FIG. 5 is an illustration of a force, pressure, or load applied to the medical sensor in accordance with an example embodiment.

FIG. 5 is an illustration of a force, pressure, or load 190 applied to medical sensor 116 in accordance with an example embodiment. FIG. 5 will refer to the elements or components of FIGS. 2-4. The illustration is a side view of medical sensor 116 being suspended above substrate 180 by supports 176 and 178. Medical sensor 116 is a part of medical device 174 configured for measuring force, pressure, or load 190. In one embodiment, medical sensor 116 is configured to measure a force, pressure, or load 190 applied by a musculoskeletal system. In one embodiment, medical sensor is within a prosthetic component or device that is placed in the musculoskeletal system. In one embodiment, the force, pressure, or load 190 is applied to a structure 170 (not shown in FIG. 5) of medical device 174 that couples to substrate 128 and overlies strain gauges 122 and 124 of medical sensor 116. Force, pressure, or load 190 is applied central to substrate 128 in the X-axis and across the entire Y-axis. Force, pressure, or load 190 causes substrate 128 to elastically deform. In one embodiment, the maximum deformation will occur at the center of substrate 128 in the X direction. The strain on substrate 128 is indicated in FIG. 5 but shown in more detail in FIG. 6. Note that the maximum strain occurs at along a center line 194 that couples through center 160 of substrate 128 of medical device 116. In one embodiment, maximum deformation or strain is approximately equal on the center line 194. Note that the strain decreases as you move farther away on either side from center line 194 on substrate 128. In one embodiment, the strain is approximately symmetrical about center line 194 at equal distances from center line 194. Increasing force, pressure, or load 190 will deform substrate 128 towards substrate 180 of medical device 174 thereby increases a resistance of strain gauges 122 and 124 of full bridge Poisson gauge 144 of medical sensor 116. Conversely, reducing force, pressure, or load 190 will reduce deformation of substrate 128 thereby reducing resistance of strain gauges 122 and 124 of full bridge Poisson gauge 144. Substrate 128 is configured to elastically deform under the force, pressure, or load. Substrate 128 is selected to elastically deform over a predetermined force, pressure, or load range.

Figure 6:
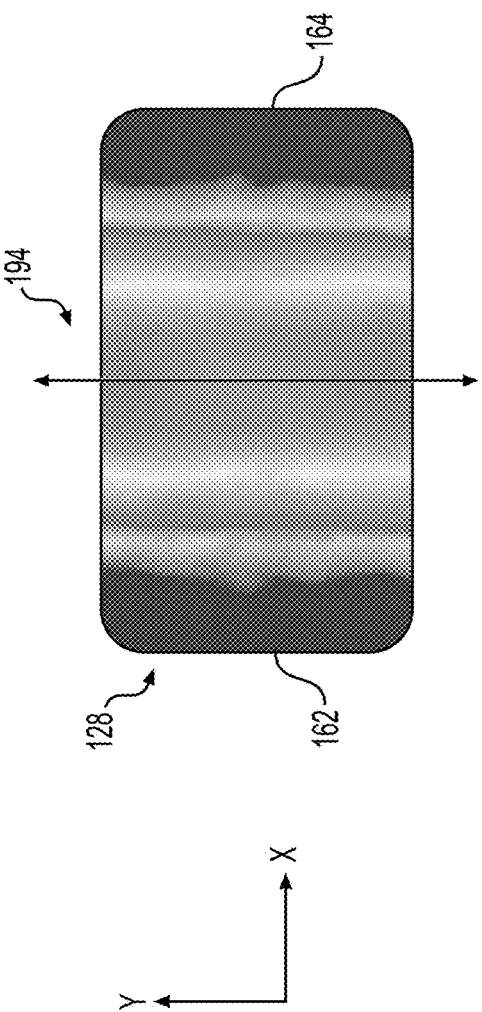
FIG. 6 is an illustration of the substrate of the medical sensor showing strain in accordance with an example embodiment.

FIG. 6 is an illustration of substrate 128 of medical sensor 116 showing strain in accordance with an example embodiment. In the example, a force, pressure, or load is applied to substrate 128 as disclosed herein above. As mentioned previously, medical sensor 116 is configured as a surface mount device for automatic pick and place to a printed circuit board. In the example, substrate 128 comprises 17-7 heat treated stainless steel. In one embodiment, substrate 128 is approximately 0.794 millimeters thick which is configured to handle loading of one hundred pounds or less. Substrate 128 can comprise a polymer, plastic, metal, or other elastically deformable material. The strain measured on substrate 128 is indicated in grey scale and the magnitude of strain is indicated in table 192. Note that the strain on substrate 128 is approximately equal in the Y-direction over a small distance in the X-direction where the origin of the X axis and Y axis is at center 160 of substrate 128 as shown in FIG. 2. Conversely, the strain changes on substrate 128 from a center line 194 of substrate 128 moving in the X-direction towards either first end 162 or second end 164 of substrate 128. In the example, the change in strain is approximately symmetrical about the center line 194. The measurement of the strain reduces from center line 194 to either first end 162 or second end 164 of substrate 128. Note that the strain measured on substrate 128 where support 176 or support 178 of structure 172 (FIG. 4) supports substrate 128 measures approximately zero. Substrate 128 supported by support structure 176 or support structure does not deform in the supported area. As mentioned previously, structure 170 of medical device 174 overlies strain gauges 122 and 124 but not strain gauges 120 and 126. This configuration of medical sensor 116 supports automated placement within medical device 174 while supporting measurement by two strain gauges per sensor for increased measurement sensitivity. In one embodiment, strain gauges 120, 122, 124, and 126 are configured to have resistances of 10,000 ohms or above to support battery operation.

Figure 7:
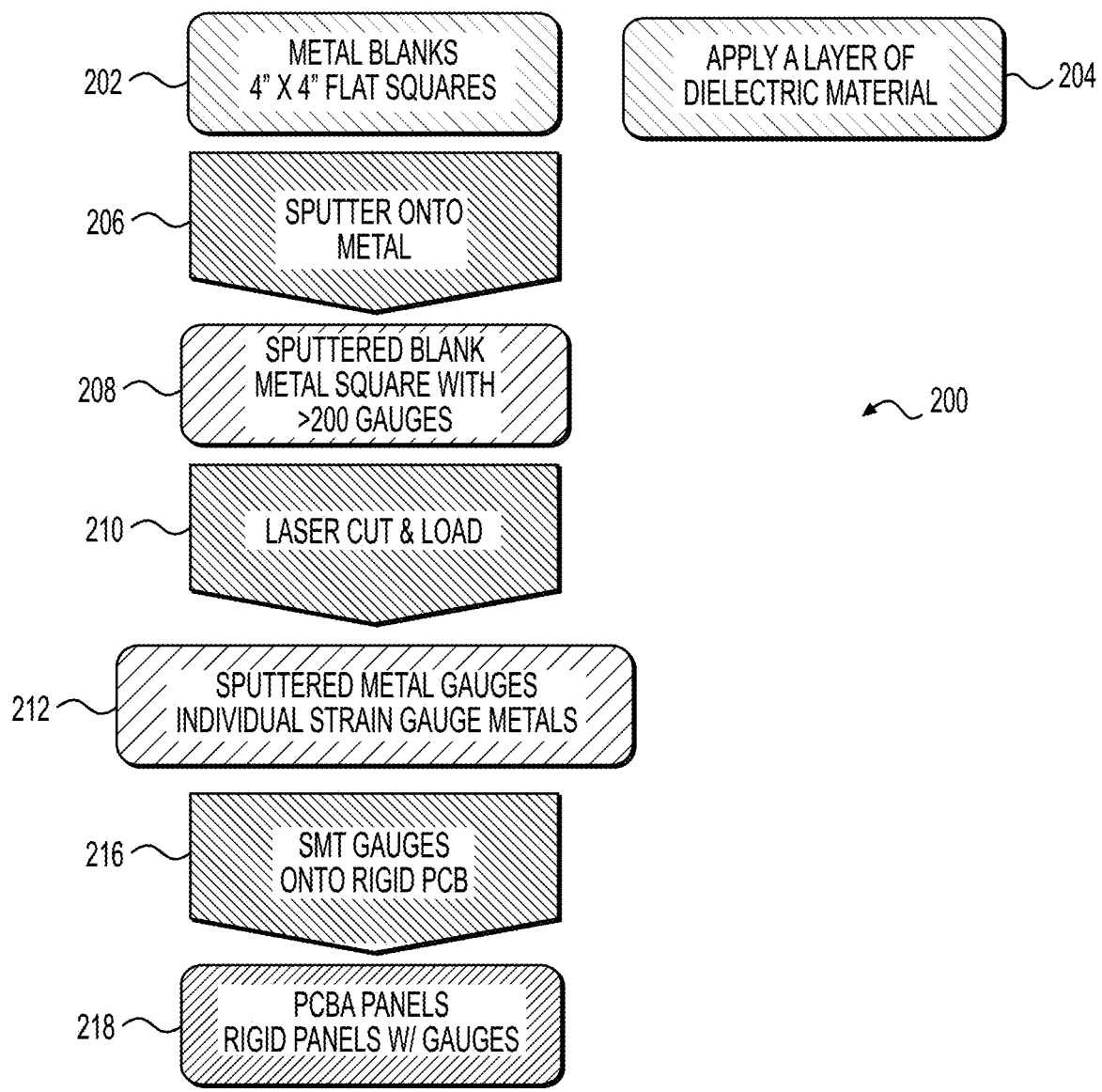
FIG. 7 is a block diagram for forming one or more of the medical sensors in accordance with an example embodiment.

FIG. 7 is a block diagram 200 for forming one or more medical sensors 116 in accordance with an example embodiment. In block diagram 200, the components and structure of medical sensor 116 of FIG. 2 and FIG. 3 will be referenced. In one embodiment, medical sensor 116 is configured to be manufactured as a surface mount device that can support an automated process of building a medical device, improved strain gauge matching, increased resistance for battery operation, reliability, performance, and lowering cost. In the example, medical sensor 116 is a full bridge Poisson strain gauge 144 comprising four strain gauges 120, 122, 124, and 126 as shown in FIGS. 2 and 3. The block diagram 200 discloses building an array of medical sensors 116 simultaneously and using an automated process to build a medical device having a plurality of medical sensors 116.

In a step 202 an array of metal blanks are provided. The metal blanks comprise a plurality of substrates 128. In one embodiment, each metal blank comprises 17-7 heat treated stainless steel in a predetermined size. In the example, each substrate is approximately 0.794 millimeters thick and configured to measure loading of approximately 100 lbs. In one embodiment, the metal blanks comprise a 4 inch by 4 inch array of 200 substrates 128. The array is designed to support handling and processing steps for forming the plurality of medical sensors 116. In a step 204, dielectric material is formed over at least one surface of substrates 128 of the array. The dielectric material is configured to couple to the plurality of substrates. In one embodiment, the dielectric material comprises polyamide. The dielectric material is a non-conductive layer configured to electrically isolate interconnect, pads, and strain gauges 120, 122, 124, and 126 from a corresponding substrate 128. In one embodiment, dielectric layer 138 can be deposited onto the array of substrates 128 simultaneously to form a uniform layer on each substrate 128. The dielectric layer will also be uniform from substrate to substrate of the plurality of substrates 128. Alternatively, a dielectric substrate can be attached to the array of substrates 128. In one embodiment, an adhesive can be used to attach the dielectric substrate to the array of substrates 128.

In a step 206, a metal layer is applied to the array of substrates 128. Metal is deposited or formed onto the plurality of substrates 128. In one embodiment, the metal is formed overlying dielectric layer 138 on the plurality of substrates 128. The metal layer can be copper, aluminum, an alloy, or other conductive metal. Alternatively, a non-metal conductive layer could also be used. In one embodiment, metal is sputtered to form the metal layer on substrates 128 of the array at the same time. The metal layer is used to form interconnect and pads overlying the array of substrates 128. In a step 210, the metal layer can be patterned using a laser to cut or remove metal. Alternatively, a patterning layer is formed overlying the metal layer to define the interconnect and pads. In one embodiment, the patterning layer can be photoresist to define protected areas where metal from the metal layer remains. An etchant is used to etch the metal not protected by the photoresist thereby leaving the patterned metal. In the example, each substrate of the array has patterned metal corresponding to interconnect and pads 130, 132, 134, and 136. A laser can also be used to cut or sever the metal blanks.

In a step 212, the strain gauges are formed overlying the dielectric layer 138. In one embodiment, the material used to form a strain gauge is a conductive material that will change resistance depending on an applied strain. In one embodiment, Nichrome is used to form strain gauges 120, 122, 124, and 126. Nichrome is an alloy of nickel and chromium that is commonly used as a resistance heating element. Nichrome will change resistance predictably under strain and can be formed into a strain gauge greater than 10K ohms for use in a battery operated medical device. Nichrome is deposited overlying the dielectric material. Similar to the process disclosed on patterning the metal to form interconnect and pads, the deposited Nichrome can be masked to define strain gauges 120, 122, 124, and 126 on each of the plurality of substrates 128. In one embodiment, etchant is used to remove Nichrome. The masked areas are protected from the etchant thereby leaving strain gauges 120, 122, 124, and 126 on dielectric layer 138. The terminals of strain gauges 120, 122, 124, and 126 are formed on corresponding metal interconnect. Nichrome formed on metal interconnect will form a contact or electrode that conducts electricity. As mentioned previously, the metal interconnect couples to strain gauges 120, 122, 124, and 126 to form the full bridge Poisson gauge 144 as shown in FIG. 3. The metal interconnect also couples to pads 130, 132, 134, and 136 for coupling the full bridge Poisson gauge 144 for voltage bias and the measurement output. The array now comprises a plurality of medical sensors 116. In one embodiment, the array of medical sensors 116 can be placed in a probing station for automated testing before being separated into individual medical sensors. No order is implied in the method. For example, strain gauges 120, 122, 124, and 126 can be formed before metal is deposited overlying dielectric layer 138 on the plurality of substrates 128. Strain gauges 120, 122, 124, and 126 are formed as disclosed herein above. The metal can then be deposited, patterned, and etched to couple to strain gauges 120, 122, 124, and 126 and to form interconnect and pads 130, 132, 134, and 136.

Medical sensors 116 are separated from one another and can be handled as a surface mount device. In an automated surface mount technology process, medical sensors 116 can be pick and placed to populate a printed circuit board. In one embodiment, medical sensors 116 are tested and placed in a tray or holder for surface mounting. In a step 216, medical sensor 116 is precisely placed onto a printed circuit board such that pads 130, 132, 134, and 136 are soldered to corresponding pads on the printed circuit board. Other components are populated on the printed circuit board during the surface mount process to form a circuit or system. In one embodiment, the circuit is configured to support a measurement process and transmit measurement data. In one embodiment, the printed circuit board is populated with two or more medical sensors 116 placed and coupled in predetermined locations on the printed circuit board.

In the step 216, at least one of the full bridge Poisson gauges 144 are coupled to a printed circuit board using surface mount technology. Referring briefly to FIG. 1, surface mount sensor 104 is shown coupling to printed circuit board 102. In one embodiment, at least three of the full bridge Poisson gauges 144 are coupled to the printed circuit board. The printed circuit board has interconnect that couples one or more full bridge Poisson gauges 144 and electrical components into an operational circuit or system. In one embodiment, the operational circuit of printed circuit board is configured to control a measurement process of the full bridge Poisson gauges 144. In one embodiment, the full bridge Poisson gauges 144 are configured to measure a load magnitude and a position of applied load. The operational circuit can be configured to transmit data from the full bridge Poisson gauges or other sensors coupled to the circuit. In a step 218, the printed circuit board assembly is completed using surface mount technology. The components and full bridge Poisson gauges 144 are coupled to the printed circuit board. The printed circuit board assembly may be placed in a furnace to reflow the solder joints for electrical and mechanical coupling. The printed circuit board assembly can then be placed or mounted within medical device 174.

Figure 8:
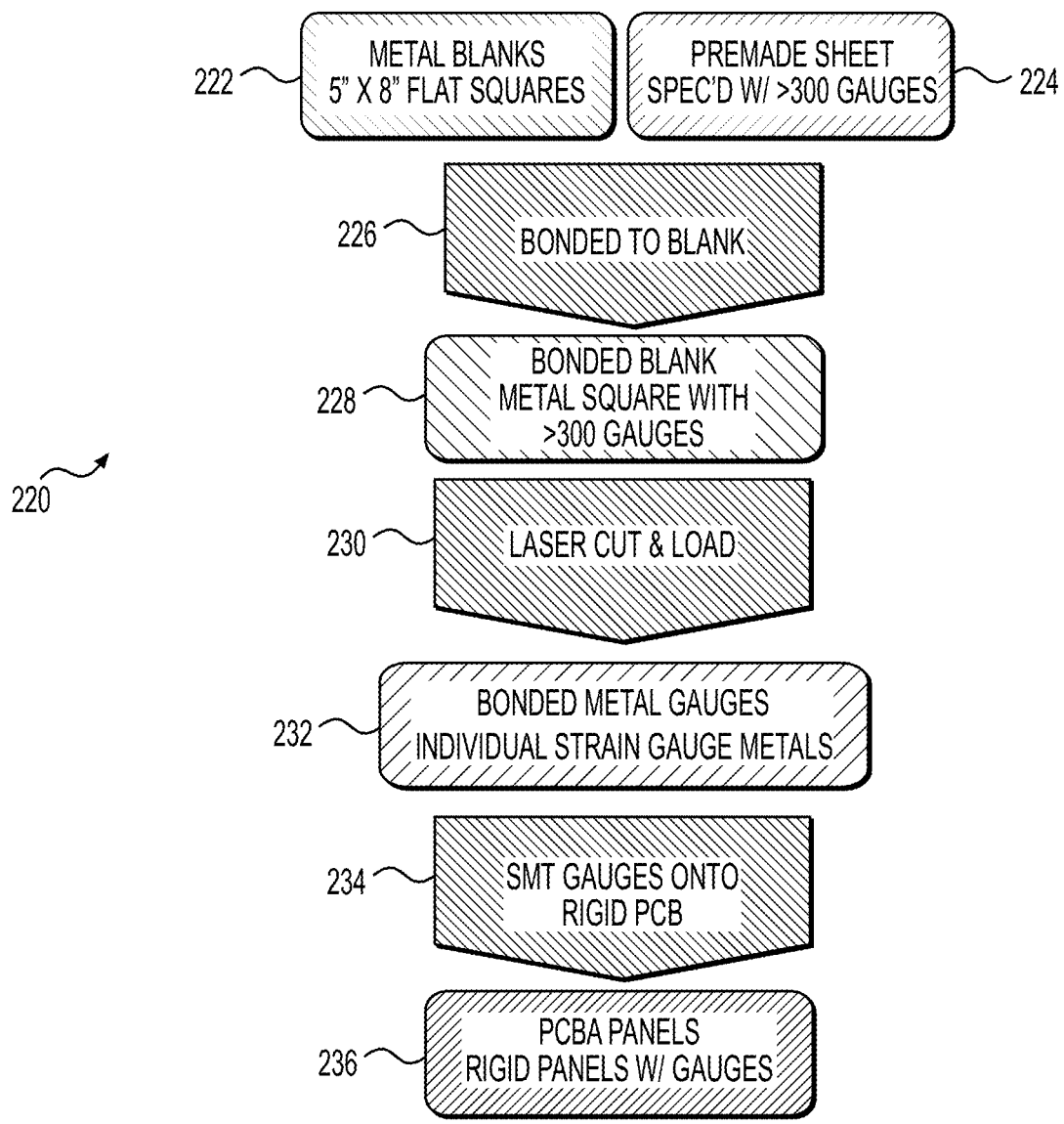
FIG. 8 is a block diagram for forming one or more of the medical sensors in accordance with an example embodiment.

FIG. 8 is a block diagram 220 for forming one or more medical sensors 116 in accordance with an example embodiment. In block diagram 220, the components and structure of medical sensor 116 of FIG. 2 and FIG. 3 will be referenced. In one embodiment, medical sensor 116 is configured to be manufactured as a surface mount device that can support an automated process of building a medical device, improved strain gauge matching, increased resistance for battery operation, reliability, performance, and lowering cost. In the example, medical sensor 116 is a full bridge Poisson strain gauge 144 comprising four strain gauges 120, 122, 124, and 126 of FIGS. 2 and 3. The block diagram 220 discloses building an array of medical sensors 116 simultaneously and using an automated process to build a medical device having a plurality of medical sensors 116.

In a step 222, an array of metal blanks is provided. The metal blanks comprise a plurality of substrates 128. In one embodiment, each metal blank comprises 17-7 heat treated stainless steel in a predetermined size. In the example, each substrate is approximately 0.794 millimeters thick and configured to measure loading of approximately 100 lbs. In one embodiment, the metal blanks comprise a 4 inch by 4 inch array of 200 substrates 128. The array of metal blanks is designed to support handling and processing steps for forming the plurality of medical sensors 116.

In a step 224, a sheet of full bridge Poisson gauges are formed. The sheet of strain gauges are formed in a separate process to control the tolerances of the deposited strain gauge metal such that strain gauges 120, 122, 124, and 126 will match more accurately as required in a medical device application. A substrate comprising a dielectric material is configured to couple to a sacrificial substrate. The sacrificial substrate is a substrate that is used to support performing processing steps on the dielectric material. In one embodiment, a polyamide substrate can be formed on or coupled to the sacrificial substrate. Polyamide is a dielectric material. The sacrificial substrate is used to support the polyamide substrate during the process of forming the strain gauges 120, 122, 124, and 126, interconnect, and pads 130, 132, 134, and 136. The sacrificial substrate can be glass, metal, a polymer, or other suitable material. In one embodiment, the dielectric material will not form a permanent or irreversible bond to the sacrificial substrate thereby supporting removal of the dielectric substrate from the sacrificial substrate. The sacrificial substrate is not used further in the process to manufacture medical sensor 116. The sacrificial substrate may be disposed of or reused to support processing another substrate. Alternatively, strain gauges 120, 122, 124, and 126 can be premade strain gauges. In one embodiment the premade strain gauges can be coupled to the sacrificial substrate.

In general, a plurality of full bridge Poisson gauges 144 (each comprising strain gauges 120, 122, 124, and 126, interconnect, and pads 130, 132, 134, and 136) are formed on the dielectric substrate and each full bridge Poisson gauge is configured to couple to a corresponding substrate 128 of plurality of substrates 128. In one embodiment, Nichrome is sputtered onto, patterned, and etched on the dielectric substrate to form strain gauges 120, 122, 124, and 126 as disclosed herein above. Similarly, the metal interconnect and pads 130, 132, 134, and 136 can be deposited, patterned, and etched on the polyamide substrate in a different or separate step. Note that the plurality of full bridge Poisson gauges 144 are formed simultaneously as an array. In one embodiment, the metal interconnect and pads can be formed of copper, aluminum, a metal, a low resistance material, or an alloy. The metal is configured to couple to the Nichrome. No order is implied in the above mentioned steps as the Nichrome can be deposited, patterned, and etched before or after the metal is deposited, patterned, and etched. The polyamide substrate is then removed from the sacrificial substrate. Thus, polyamide substrate removed from the sacrificial substrate comprises a plurality of full bridge Poisson gauges 144 that corresponds to the plurality of substrates 128. Each full bridge Poisson gauge 144 comprises strain gauges 120, 122, 124, and 126, interconnect, and pads 130, 132, 134, and 136 configured for supporting surface mount technology. Alternatively, the premade strain gauges can be provided.

In a step 226, the polyamide sheet is coupled to the array of metal blanks such that each full bridge Poisson gauge 144, interconnect, and pads 130, 132, 134, and 136 is aligned to a corresponding metal blank of the array of metal blanks. In one embodiment, an adhesive can be used to couple the polyamide sheet to the array of metal blanks. The polyamide substrate of the pre-manufactured sheet isolates or prevents electrical coupling of full bridge Poisson gauges 144, interconnect, and pads 130, 132, 134, and 136 to a corresponding metal blank (e.g. substrate 128). An adhesive can be applied between the polyamide sheet and the array of metal blanks. In one embodiment, the array of metal blanks and the polyamide sheet are placed in an oven. The adhesive, polyamide sheet, and the array of metal blanks are heated for a predetermined time to cure the adhesive such that polyamide sheet couples to the array of metal blanks. In one embodiment, the adhesive is configured to match the expansion coefficient of the metal used in the array of metal blanks. In a step 228, the bonded blank can be handled after the adhesive is cured and comprises a plurality of full bridge Poisson gauges 144. In a step 230, medical sensors 116 are separated from one another. In one embodiment, medical sensors 116 can be laser cut, tested, calibrated, and loaded to be used in an automated surface mount technology system. In a step 232, medical sensors 116 after being separated from one another can be placed in a tray for automated pick up, placement, and soldering of medical sensors 116 to a printed circuit board. In one embodiment, medical sensors 116 are full bridge Poisson gauge 144 comprising a metal such as Nichrome formed on a dielectric substrate that is bonded to a substrate 128 comprising metal. The metal substrate is configured to induce strain on the full bridge Poisson gauge 144 under load. The force, pressure, or load applied to the metal substrate relates to the resistance measured by full bridge Poisson gauge 144. In one embodiment, the resistance of full bridge Poisson gauge 144 is converted to a voltage such that the voltage relates to the force, pressure, or load applied to the metal substrate. In an alternate embodiment, premade strain gauges can be coupled to the array of metal blanks. The premade strain gauges will have the orientation as shown in FIG. 2.

In a step 234, at least one of the full bridge Poisson gauges 144 are coupled to a printed circuit board using surface mount technology. Referring briefly to FIG. 1, surface mount sensor 104 is shown coupling to printed circuit board 102. In one embodiment, at least three of the full bridge Poisson gauges 144 are coupled to the printed circuit board. The printed circuit board has interconnect to couple full bridge Poisson gauges 144 and components in an operational circuit. In one embodiment, the operational circuit of printed circuit board is configured to control a measurement process of full bridge Poisson gauges 144. In one embodiment, full bridge Poisson gauges 144 are configured to measure a load magnitude and a position of applied load at predetermined locations. The operational circuit can be configured to transmit data from the full bridge Poisson gauges or other sensors coupled to the circuit. In a step 236, the printed circuit board assembly is completed using surface mount technology. The components and full bridge Poisson gauges 144 are coupled to the printed circuit board. The printed circuit board assembly may be placed in a furnace to reflow the solder joints for electrical and mechanical coupling. The printed circuit board assembly can then be placed or mounted within medical device 174.

Figure 9:
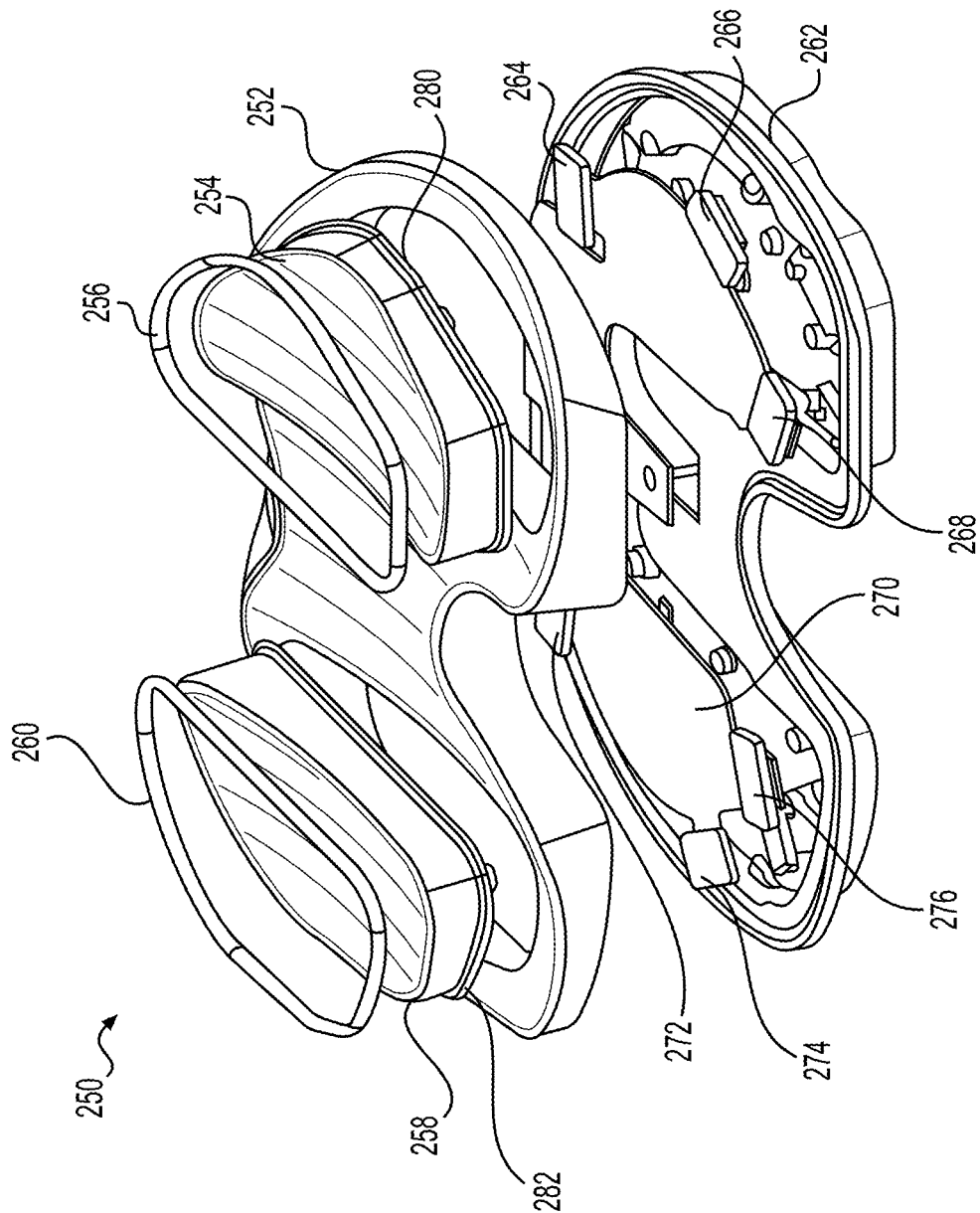
FIG. 9 is an illustration of a medical device in accordance with an example embodiment.

FIG. 9 is an illustration of a medical device 250 in accordance with an example embodiment. Medical device 250 is a device for measuring loading applied by the musculoskeletal system. Medical device 250 couples to the musculoskeletal system and can be a tool, equipment, device, or structure configured to measure an applied force, pressure, or load. In one embodiment, medical device 250 can be a module configured to couple to a tool, device, or prosthetic component to support a force, pressure, or load measurement. In the example, medical device 250 is a prosthetic component. More specifically, medical device 250 as shown is an insert of a knee prosthetic joint. The insert is a prosthetic component that couples between a femoral prosthetic component (coupled to a femur) and a tibial prosthetic component (coupled to a tibia). The condyles of the femoral prosthetic component couple to surfaces of the insert to support movement under musculoskeletal loading. In one embodiment, the insert is a trialing device. In one embodiment, medical device 250 is configured to measure loading applied by the musculoskeletal system on a medial side and a lateral side of a knee joint. The quantitative measurement data from medical device 250 as a trialing device is used to adjust parameters such loading, balance, and position of applied load on the medial and lateral sides of the insert. The quantitative measurement data is sent to a computer in view of a surgeon and surgical team that can be viewed in real-time as adjustments are made. Medical device 250 is removed after the measured parameters are within a predetermined range based on clinical evidence for a knee joint and a final insert (identical in shape and size) is fitted within the knee joint. In one embodiment, medical device 250 is used to support balancing the knee joint such that the loading applied to the medial and lateral side of the insert is at a predetermined ratio. Alternatively, medical device 250 can be integrated in a tool such as a knee tensor to provide position of applied load and load magnitude measurements or as a separate module that can be placed in equipment for measurement purposes and then removed.

Reference to structure or elements in FIGS. 1-7 will be used to illustrate measuring force, pressure, or load in medical device 250. Medical device 250 comprises a structure 252, a structure 262, surface module, 254, surface module 258, seal 256, seal 260, printed circuit board 270, and full bridge Poisson gauges 264, 266, 268, 272, 274, and 276. Structure 252 and structure 262 couple together to form a housing of medical device 250 that is hermetically sealed. Surface module 254 and surface module 258 provide an articular surface for supporting knee motion as the knee joint is tested. Surface module 254 and surface module 258 couple to the condyles of the femur or the condyles of a femoral prosthetic component. Surface modules 254 and 258 fit within openings in structure 252. O-ring 256 seals surface module 254 to structure 252 to maintain hermeticity of medical device 250. Similarly, O-ring 260 seals surface module 258 to structure 252 to maintain hermeticity of medical device 250. In one embodiment, O-rings 256 and 260 respectively support movement of surface module 254 and surface module 258 when loaded by the musculoskeletal system. The movement of surface modules 254 and 258 is needed flex the substrates of full bridge Poisson gauges 264, 266, 268, 272, 274, or 276.

Full bridge Poisson gauges 264, 266, and 268 couple to printed circuit board 270 and are configured to measure loading applied to surface module 254. Full bridge Poisson gauges 264, 266, and 268 are placed at vertexes of a polygon. The position of full bridge Poisson gauges 264, 266, and 268 are known on printed circuit board 270 and relative to a surface of surface module 254. Similarly, full bridge Poisson gauges 272, 274, and 276 couple to printed circuit board 270 and are configured to measure loading applied to surface module 258. Full bridge Poisson gauges 272, 274, and 276 are placed at vertexes of a polygon. The position of full bridge Poisson gauges 272, 274, and 276 are known on printed circuit board 270 and relative to a surface of surface module 258.

Electronic components couple to printed circuit board 270. The electronic components are electrically coupled together using one or more layers of interconnect on or in printed circuit board 270 to form a circuit or system. In one embodiment, the system is configured to generate measurement data from one or more sensors coupled to the circuit and transmit the measurement data to a computer or interface that is separate from medical device 250. In general, each full bridge Poisson gauge is configured to generate a load measurement. A computer receives the load magnitude at each location of the polygon and calculates a position of applied load on the surface of the corresponding surface module from the measurement data. The computer will also calculate the load magnitude at the position of applied load on the surface of the corresponding surface module. In one embodiment, medical device 250 can provide the measurement data in real-time to track changes in position of applied load and load magnitude over a range of motion.

Full bridge Poisson gauges 264, 266, 268, 272, 274, and 276 are formed as described herein above as surface mount technology devices that supports accurate placement on printed circuit board 270 using an automated manufacturing process. Precise placement of full bridge Poisson gauges 264, 266, 268, 272, 274, and 276 is important because printed circuit board 270 and full bridge Poisson gauges 264, 266, 268, 272, 274, and 276 couple to structure 262, surface module 254, and surface module 258 at predetermined locations. Misalignment will result in inaccurate measurement results, reliability issues, or device failure. There are two or more alignment features on structure 262 that align and retain printed circuit board 270 to structure 262. The placement of printed circuit board 270 to structure 262 aligns full bridge Poisson gauges 264, 266, 268, 272, 274, and 276 to corresponding supports formed in structure 262 that suspends the sensors over a cavity to support flexing of the substrate under load. Thus, full bridge Poisson gauges 264, 266, 268, 272, 274, and 276 are supported, aligned, and retained at predetermined locations of structure 262 and surface mounted to printed circuit board 270.

Structure 252 aligns and couples to structure 262. Surface module 254 fits within an opening in structure 252. In one embodiment, surface module 254 has a retaining lip 280. O-ring 256 is placed around surface module 254 and a portion of O-ring 256 is configured to be held in place by retaining lip 280. In one embodiment, surface module 254 will be stopped from being pushed further in the opening of structure 252 when O-ring 256 couples between retaining lip 280 and the corresponding lip on structure 252 within the opening. O-ring 256 will compress between structure 252 and surface module 254 to hermetically seal the opening in structure 252. Furthermore, O-ring 256 supports movement of surface module 254 while maintaining the hermetic seal during an application of a force, pressure, or load to full bridge Poisson gauges 264, 266, and 268. In one embodiment, a first region, a second region, and a third region extends from surface module 254 to couple respectively to full bridge Poisson gauges 264, 266, and 268. In one embodiment, the first region, the second region, and the third region correspond to predetermined locations on the surface of surface module 254. The predetermined locations are used in the calculation of the position of applied load and the load magnitude at the position of applied load. In one embodiment, the first, second, and third regions each have a predetermined area that is configured to couple respectively to predetermined areas of full bridge Poisson gauges 264, 266, and 268.

Similarly, surface module 258 fits within an opening in structure 252. In one embodiment, surface module 258 has a retaining lip 282. O-ring 260 is placed around surface module 258 and a portion of O-ring 260 is configured to be held in place by retaining lip 282. In one embodiment, surface module 258 is pushed within the opening in structure 252 until O-ring 260 couples to a corresponding retaining lip on structure 252. In one embodiment, surface module 258 will be stopped from being pushed further in the opening of structure 252 when O-ring 260 couples between retaining lip 282 and the corresponding lip on structure 252 within the opening. O-ring 260 will compress between structure 252 and surface module 258 to hermetically seal the opening in structure 252. Furthermore, O-ring 260 supports movement of surface module 258 while maintaining the hermetic seal during an application of a force, pressure, or load to full bridge Poisson gauges 272, 274, and 276. In one embodiment, a first region, a second region, and a third region extends from surface module 258 to couple respectively to full bridge Poisson gauges 272, 274, and 276. In one embodiment, the first region, the second region, and the third region correspond to predetermined locations on the surface of surface module 258. The predetermined locations are used in the calculation of the position of applied load and the load magnitude at the position of applied load. In one embodiment, the first, second, and third regions of surface module 258 each have a predetermined area that is configured to couple respectively to predetermined areas of full bridge Poisson gauges 272, 274, and 276. This will be disclosed in greater detail herein below.

Figure 10:
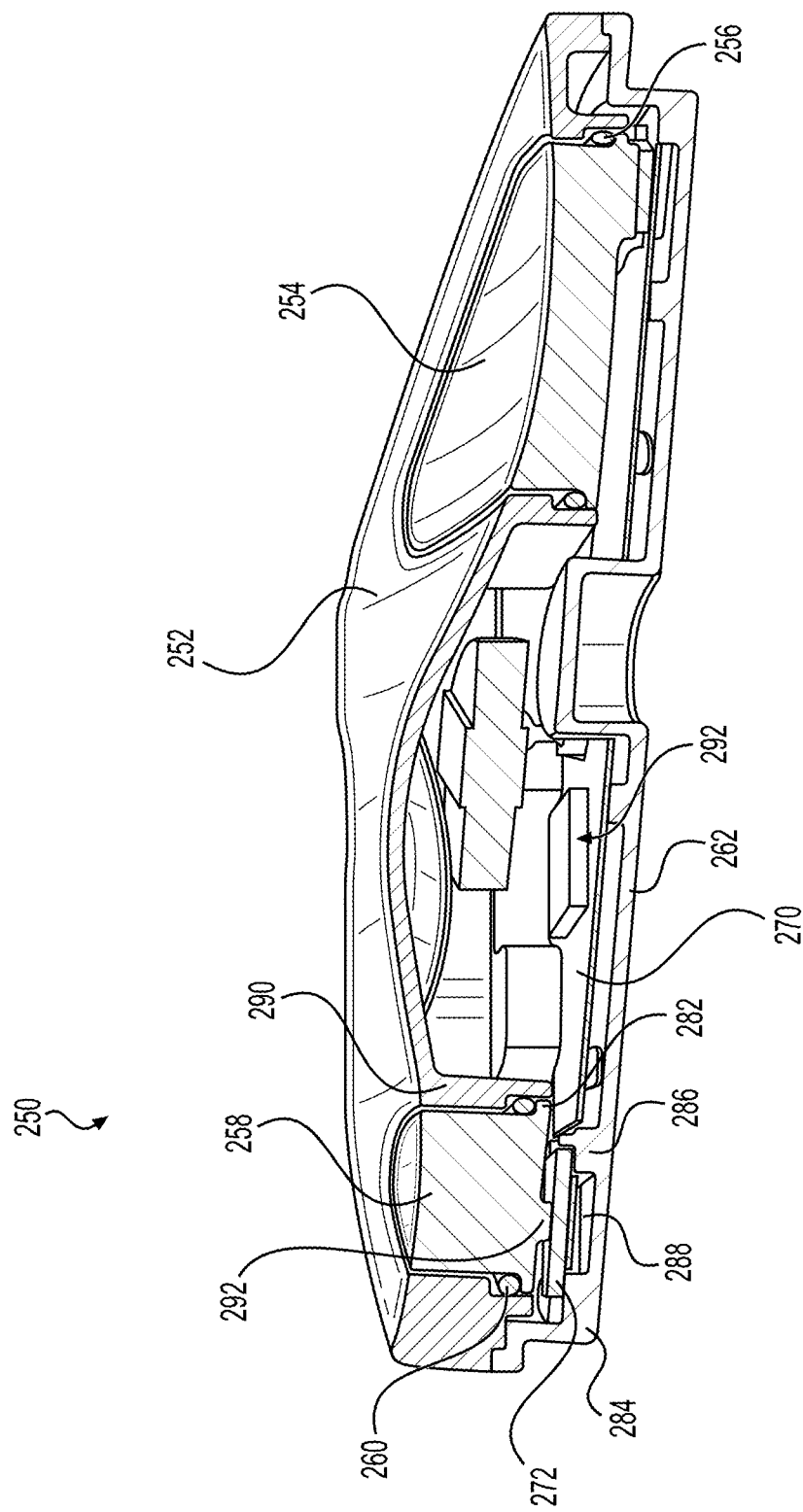
FIG. 10 is a cross-sectional view of the medical device illustrating the full bridge Poisson bridge coupled between a surface module and a structure in accordance with an example embodiment.

FIG. 10 is a cross-sectional view of medical device 250 illustrating full bridge Poisson gauge 272 coupled between surface module 258 and structure 262 in accordance with an example embodiment. In particular, the cross-sectional view illustrates how the surface mounted full bridge Poisson gauge 272 is placed into medical device 250. Surface mounted full bridge Poisson gauge 272 is equivalent to medical sensor 116 disclosed in FIGS. 2-6. Referring briefly to FIG. 4, substrate 128 having a sensor array 118 is coupled to medical device 174. Substrate 128 is supported by support 176 and support 178 on a sensored side of substrate 128. Structure 170 applies a force, pressure, or load to substrate 128 on a non-sensored side of substrate 128. In one embodiment, structure 170 applies the force, pressure, or load to active strain gauges of the sensor array while the non-active strain gauges of the sensor array have minimal or no force, pressure, or load applied. Full bridge Poisson gauges 264, 266, and 268 of medical device 250 coupled between surface module 254 and structure 262 is coupled similar to sensor array 118 of FIG. 4. Similarly, full bridge Poisson gauges 272, 274, and 276 coupled between surface module 258 and structure 262 is coupled similar to sensor array 118 of FIG. 4. This is shown in detail for full bridge Poisson gauge 272 in the cross-sectional view discussed herein below.

Full bridge Poisson gauge 272 is surface mounted to printed circuit board 270. Full bridge Poisson gauge 272 is supported by at a first end by support 284 of structure 262 and at a second end by support 286 of structure 262. One or more retaining features align and retain full bridge Poisson gauge 272 and printed circuit board 270 to structure 262. Full bridge Poisson gauge 272 and a portion of printed circuit board 270 are suspended over a cavity 288 in structure 262. Surface module 258 includes a region 292 that is configured to couple to full bridge Poisson gauge 272. In one embodiment, region 292 couples to a non-sensored side of the substrate of full bridge Poisson gauge 272. Region 292 of surface module 258 has a predetermined area configured to couple to a predetermined area of full bridge Poisson gauge 272. In one embodiment, the predetermined area of region 292 relates to applying a force, pressure, or load to the active strain gauges of full bridge Poisson gauge 272. In one embodiment, the predetermined area of region 292 does not overlie the non-active strain gauges of full bridge Poisson gauge 272. O-ring 260 forms the hermetic seal between structure 252 and surface module 258. Retaining lip 282 of surface module 258 and retaining lip 290 of structure 252 supports retention of O-ring 260 in a predetermined location. O-ring 260 comprises a compressible material such as PTFE, Neoprene, Rubber, Fluorocarbon, or silicone that supports movement of surface module 258 under the force, pressure, or load.

A force, pressure, or load applied to surface module 258 couples a portion of the force to full bridge Poisson gauge 272. The remaining force, pressure, or load is applied to full bridge Poisson gauges 274 and 276. The location of region 292 of surface module 258 corresponds to a predetermined location on the surface of surface module 258. Electronic circuitry 292 coupled to printed circuit board 270 is configured to control a measurement process and transmit measurement data. In general, the measurement data is transmitted to a computer. The computer receives the measurement data from full bridge Poisson gauges 264, 266, 268, 272, 274, and 276. The computer also has the corresponding locations of the full bridge Poisson gauges relative to the surface of surface modules 254 or 258. The computer can then calculate the position of applied load and the magnitude of the applied load from the measurement data from the three full bridge Poisson gauges that correspond to the surface module. The measurement data is provided in real-time such that changes in measured force, pressure, or load results in a change in the position of applied load and the load magnitude at the position of applied load. In one embodiment, the position of applied load and the load magnitude is displayed on a display coupled to the computer.

Referring to FIGS. 2, 3, 9, and 10, medical sensor 116 is a surface mount device configured to use an automated surface mount technology system to mount medical sensor 116 to a printed circuit board 270. Medical sensor 116 comprises a substrate 128. Substrate 128 is configured to flex in a predetermined direction when placed in a medical device. Substrate 128 has a center 160 and a centerline. The centerline goes through center 160 and can be parallel to the X-axis or the Y-axis. A dielectric layer 138 overlies substrate 128. The dielectric layer 138 can also be a dielectric substrate coupled to substrate 128. A first strain gauge 120, a second strain gauge 122, a third strain gauge 124, and a fourth strain gauge 126 overlie dielectric layer 138. Second strain gauge 122 and third strain gauge 124 are configured to measure strain in a predetermined direction. Second strain gauge 122 and third strain gauge 124 are placed symmetrical about center 160 or the centerline of substrate 128. In one embodiment, a center of second strain gauge 122 and a center of third strain gauge 124 are placed on the centerline. In the example, the center of strain gauge 122 and the center of third strain gauge 124 are placed on the centerline parallel to the Y-axis that couples through the center 160 of substrate 128.

Strain gauges 120, 122, 124, and 126 are configured in a full bridge Poisson gauge 144. In the full bridge Poisson strain gauge 144, second strain gauge 122 and third strain gauge 124 are active whereby they are used to measure a force, pressure, or load applied to substrate 128. In one embodiment, the force, pressure, or load is applied to center 160 of substrate 128 or an area of substrate 128 corresponding to center 128. First strain gauge 120 and fourth strain gauge 126 are non-active in full bridge Poisson strain gauge 144. In the example, first strain gauge 120 and fourth strain gauge 126 are aligned to measure strain on substrate 128 in the Y-axis direction or perpendicular the active strain gauges. Referring briefly to FIG. 4, the application of a force, pressure, or load in medical device 174 as disclosed results in little or no strain to be measured by first strain gauge 120 and fourth strain gauge 126 such that first strain gauge 120 and fourth strain gauge 126 are non-active.

Interconnect is formed overlying dielectric layer 138. Similarly, a plurality of pads 130, 132, 134, and 136 are formed overlying dielectric layer 138. The interconnect and plurality of pads 130, 132, 134, and 136 are formed of a metal such as copper, aluminum, or an alloy. Plurality of pads 130, 132, 134, and 136 are surface mount technology (SMT) pads. The interconnect is configured to couple first strain gauge 120, second strain gauge 122, third strain gauge 124, and fourth strain gauge 126 into full bridge Poisson strain gauge 144. The interconnect is further configured to couple the full bridge Poisson gauge to plurality of pads 130, 132, 134, and 136. Plurality of pads 130, 132, 134, and 136 are used in a surface mount technology process to couples full bridge Poisson gauge 144 to a printed circuit board in an automated pick, place, and solder process. In general, the metallization of first strain gauge 120, second strain gauge 122, third strain gauge 124, and fourth strain gauge 126 is of a different metal than the metallization of the interconnect. The strain gauges comprise a measurable resistive material while the interconnect and plurality of pads comprise a low resistance metal.

In one embodiment, first strain gauge 120, second strain gauge 122, third strain gauge 124, and fourth strain gauge 126 are formed from sputtered metal on dielectric layer 138. After a sputtered metal layer is deposited overlying dielectric layer 138, the sputtered metal is patterned, for example using photoresist and etched to remove sputtered metal in predetermined locations to form first strain gauge 120, second strain gauge 122, third strain gauge 124, and fourth strain gauge 126. In one embodiment, dielectric layer 138 comprises polyamide. Dielectric layer 138 can be deposited overlying substrate 128 or formed in a sheet or substrate that couples to substrate 128. Typically, substrate 128 comprises a flexible material such as a polymer, metal, or alloy. In one embodiment, substrate 128 comprises 17-7 heat treated stainless steel and is 0.80 millimeters or less in thickness.

Referring briefly to FIG. 4, medical device 174 has a support 176 and a support 178 configured to couple respectively to a first end and a second end of substrate 128 of medical sensor 116. A force, pressure, or load is applied to a structure 170 of medical device 174 is distributed across a predetermined area of substrate 128. The force, pressure, or load applied to medical sensor 174 is configured to have maximum strain in proximity to the center or centerline of substrate 128 that corresponds to the location of second strain gauge 122 and third strain gauge 124. Second strain gauge 122 and third strain gauge 124 are configured to measure strain on substrate 128 that can be related to the force, pressure, or load applied to structure 170 of medical device 174.

Figure 11:
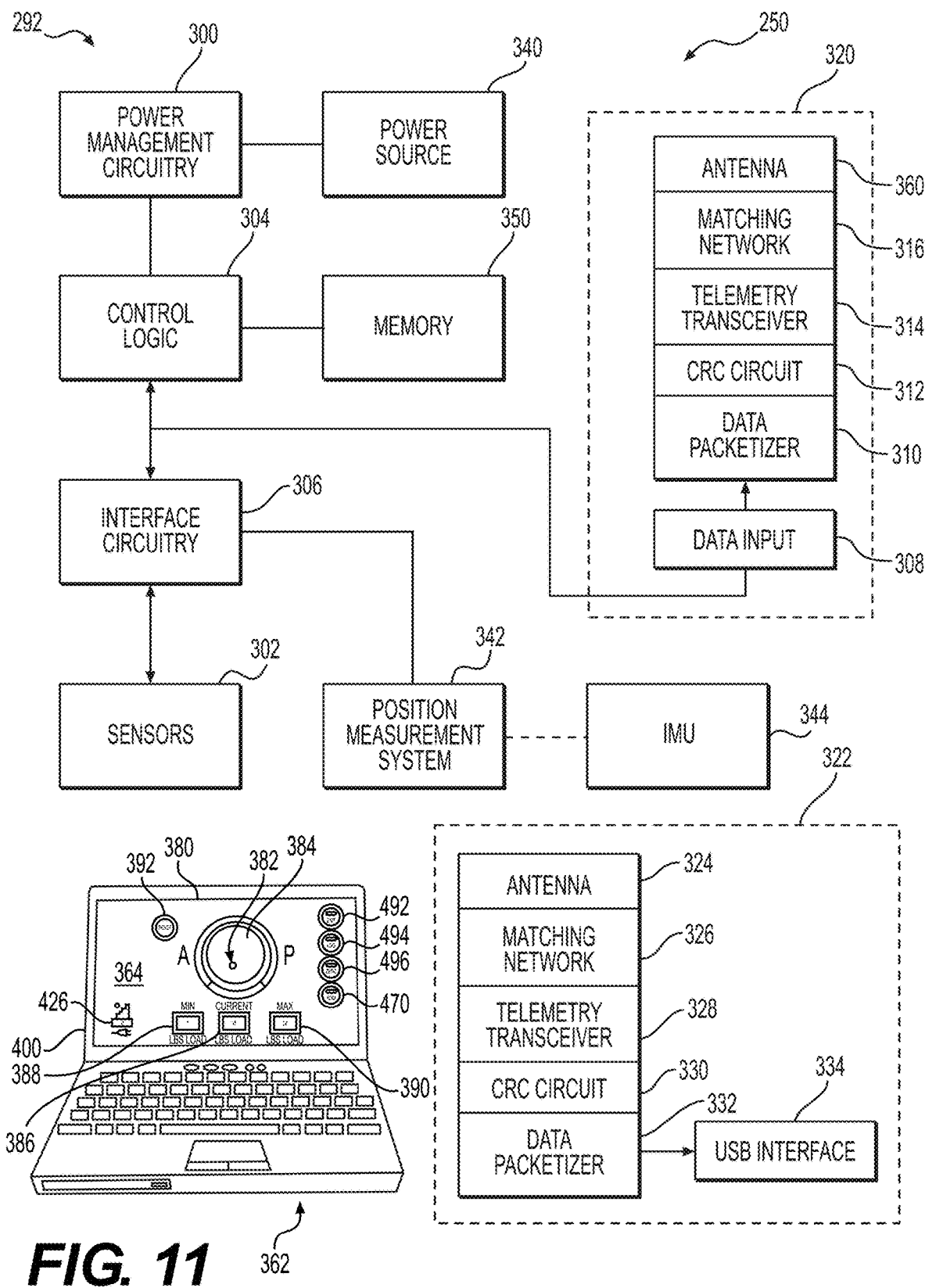
FIG. 11 is a block diagram of electronic circuitry in the measurement device in accordance with an example embodiment.

FIG. 11 is a block diagram of electronic circuitry 292 in measurement device 250 in accordance with an example embodiment. In general, electronic circuitry 292 couples to one or more sensors to measure one or more parameters. Components of FIGS. 1-5 and 7-8 may be referred to in the discussion herein below to relate operation of medical device 250 to electronic circuitry 292. The sensors can measure parameters such as, height, length, width, tilt/slope, position, orientation, load magnitude, force, pressure, contact point location, displacement, density, viscosity, pH, light, color, sound, optical, vascular flow, visual recognition, humidity, alignment, position, rotation, inertial sensing, turbidity, bone density, fluid viscosity, strain, angular deformity, vibration, torque, elasticity, motion, acceleration, infection, pain, and temperature to name but a few. In the example, electronic circuitry 292 is configured to control a measurement process, receive measurement data from sensors 302, receive measurement data from position measurement system 342, and transmit the measurement data to computer 362 for further analysis and feedback. More specifically, sensors 302 measure a force, pressure, or load at predetermined locations of surface module 254 or surface module 258. Sensors 302 at the predetermined locations underlying surface modules 254 and 258 comprise full bridge Poisson gauges 264, 266, 268, 272, 274, and 276 as shown in FIG. 9. Position measurement system 342 measures position, movement, rotation, velocity, acceleration, or distance. In one embodiment, position measurement system comprises an inertial measurement unit (IMU) 344 configured to measure 9 degrees of freedom. IMU 344 can comprise one or more inertial sensors. In one embodiment, sensors 302 and position measurement system 342 is housed in medical device 250. Sensors 302 can comprise other sensors coupled to electronic circuitry 292.

Electronic circuitry 292 comprises power management circuitry 300, control logic 304, memory 350, interface circuitry 306, position measurement system 342, and wireless communication circuitry 320. A power source 340 couples to electronic circuitry 292 to power a measurement process. Power source 340 can be an inductor, super capacitor, storage cell, wired power, wireless power, solar cell, energy harvesting device, or other energy storage medium. In one embodiment, power source 340 comprises one or more batteries. Electronic circuitry 292 further includes a transceiver that can be positioned on or within, or engaged with, or attached or affixed to or within, a wide range of physical systems including, but not limited to instruments, equipment, devices, prosthetic components, or other physical systems for use on or in human bodies and configured for sensing and communicating parameters of interest in real time. The components of electronic circuitry 292 are coupled together to form an electronic system using one or more layers of interconnect on printed circuit board 270. Flexible interconnect can be used to couple electronic circuitry 292 to sensors 302 that are remotely located.

Electronic circuitry 292 can be configured to provide two-way communication between medical device 250 and computer 362. In one embodiment, medical device 250 provides quantitative measurement data related to a knee joint installation. Medical device 250 is configured to provide quantitative measurement data related to load magnitude, position of applied load, position, and rotation for the medial or lateral side of the knee in real-time. The measurement data from medical device 250 is used by computer 362 in a kinematic assessment to support installation of prosthetic components to ensure optimal loading, balance, stability, alignment, and range of motion, whereby improved performance and reliability is the result based on clinical evidence.

Power source 340 provides power to electronic circuitry 292 and sensors 302. The power source 340 can be temporary or permanent. In one embodiment, the power source is not rechargeable. Medical device 250 is disposable after a single use and the power in the batteries are insufficient for a second surgery. In one embodiment, medical device 250 would be destroyed or disposed of after being used. Alternatively, power source 340 could be rechargeable to support reuse. Medical device 250 would be sterilized before each use. Charging of power source 340 can comprise wired energy transfer or short-distance wireless energy transfer. A charging power source to recharge power source 340 can include, but is not limited to, a battery or batteries, an alternating current power supply, a radio frequency receiver, an electromagnetic induction coil, a photoelectric cell or cells, a thermocouple or thermocouples, or a transducer energy transfer. In one embodiment, energy transfer to power source 340 could be allowed for the single application scenario if power source 340 has insufficient energy to finish the surgery. Furthermore, medical device 250 can utilize power management circuitry 300 to minimize the power drain of power source 340 while in use or when electronic circuitry 292 is idling. A charging operation can be controlled by power management circuitry 300 within electronic circuitry 292. In one embodiment, power management circuit 300 supports operation of medical device 250 during charging thereby allowing the surgery to continue if a low charge on power source 340 is detected. For example, power can be transferred to the batteries, capacitive energy storage device, or inductive energy storage device by way of efficient step-up and step-down voltage conversion circuitry. This conserves operating power of circuit blocks at a minimum voltage level to support the required level of performance.

Power management circuitry 300 is configured to operate under severe power constraints. In one embodiment, power management circuitry 300 controls power up, power down, and minimizes power usage during operation. The power management circuitry 300 is configured to reduce power dissipation during operation of the system. The power management circuitry 300 can turn off or reduce the power delivered to circuits that are not being used in a specific operation. Similarly, if the system is idle and not being used, the power management circuitry 300 can put other unused circuitry in a sleep mode that awakens prior to the next measurement being made. Power management circuitry 300 can include one or more voltage regulation circuits that provide a plurality of different stable voltages to electronic circuitry 292 and sensors 302.

In one configuration, a charging operation of power source 340 can further serve to communicate downlink data to electronic circuitry. For instance, downlink control data can be modulated onto the energy source signal and thereafter demodulated from an inductor in electronic circuitry 230. This can serve as a more efficient way for receiving downlink data instead of configuring an internal transceiver within electronic circuitry 230 for both uplink and downlink operation. As one example, downlink data can include updated control parameters that medical device 250 uses when making a measurement, such as external positional information or for recalibration purposes. It can also be used to download a serial number or other identification data.

Control logic 304 controls a measurement process or sequence that engages sensors 302, converts the measurement data into a useable format, and transmits the measurement information. Control logic 304 can comprise digital circuitry, a microcontroller, a microprocessor, an ASIC (Application Specific Integrated Circuit), a DSP (Digital Signal Processing), a gate array implementation, a standard cell implementation, and other circuitry. Control logic 304 is configured to store measurement data, software routines, diagnostics/test routines, calibration data, calibration algorithms, workflows, and other information or programs in memory 350 In one embodiment, measurement data from one or more sensors may be continuously enabled and sampled periodically to memory 350. Control logic 304 couples to memory 350 and is configured to store and retrieve information from memory 350. Control logic 304 controls the measurement process, stores the measurement data in memory 350, or transmits the measurement data in real-time. Control logic 304 can include dedicated ports that couple to a sensor to continuously receive measurement data or receive updated measurements at high sample rates. Alternatively, control logic 304 can select a sensor to be measured. For example, multiple sensors can be coupled to control logic 304 via a multiplexer. Control logic 304 controls which sensor is coupled through the multiplexer to sample and output the measurement data. Multiplexed measurement data works well when the measurement data is not critical or can be sampled occasionally as needed. Control logic 304 can also select and receive measurement data from different sensors in a sequence or simultaneously through parallel channels. Control logic 304 can be configured to monitor the measurement data from a sensor but transmit measurement data only when a change occurs in the measurement data. Furthermore, control logic 304 can modify the measurement data prior to transmitting the measurement data to computer 362. For example, the measurement data can be corrected for non-linearity of the sensor using calibration data stored in memory. In one embodiment, a microcontroller with Bluetooth low energy (BLE) is used with an analog to digital converter to convert analog values to digital.

Interface circuitry 306 couples between sensors 302 and control logic 304. Interface circuitry 306 supports conversion of a sensor output to a form that can be received by computer 362. Interface circuitry 306 comprises digital circuitry and analog circuitry. The analog circuitry can include multiplexers, amplifiers, buffers, comparators, filters, passive components, analog to digital converters, and digital to analog converters to name but a few. In one embodiment interface circuitry 306 uses one or more multiplexers to select a sensor for providing measurement data to control logic 304, memory 350, or wireless communication circuitry 320. Control logic 304 is configured to provide control signals that enable the multiplexer to select the sensor for measurement. Typically, at least one analog to digital conversion or digital to analog conversion of the measurement data occurs via the interface circuitry 306.

Sensors 302 couple through interface circuitry 306 to memory 350. Alternatively, interface circuitry 306 can couple directly to circuitry for transmitting measurement data as it is measured. The physical parameter or parameters of interest measured by sensors 302 are force, pressure, or load as disclosed herein but sensors 302 can further include other sensors that measure height, length, width, tilt/slope, position, orientation, load magnitude, force, pressure, contact point location, displacement, density, viscosity, pH, light, color, sound, optical, vascular flow, visual recognition, humidity, alignment, rotation, inertial sensing, turbidity, bone density, fluid viscosity, strain, angular deformity, vibration, torque, elasticity, motion, and temperature. Often, a measured parameter is used in conjunction with another measured parameter to make a kinetic and qualitative assessment. In joint reconstruction, portions of the musculoskeletal system are prepared to receive prosthetic components. Preparation includes bone cuts or bone shaping to mate with one or more prosthesis. Parameters can be evaluated relative to orientation, stability, alignment, impingement, direction, displacement, or position as well as movement, rotation, or acceleration along an axis or combination of axes by wireless sensing modules or devices positioned on or within a body, instrument, appliance, vehicle, equipment, or other physical system.

Sensors 302 can directly or indirectly measure a parameter of interest. For example, a load sensor in medical device 250 can comprise a strain gauge, a full bridge Poisson gauge, a capacitor, a piezo-sensor, or a MEMs sensor. Measuring load with a full bridge Poisson gauge is an indirect form of sensing as the strain measurement of the full bridge Poisson gauge will change with the amount of loading applied to a substrate of the load sensor. The resistive or voltage measurement data from the full bridge Poisson gauge can be sent to computer 362 for further processing. In one embodiment, computer 362 can include software and calibration data related to the full bridge Poisson gauge. Alternatively, the calibration data can be stored with electronic circuitry 292 which is then downloaded to computer 363 prior to a measurement. The load measurement data can be converted from the strain measurements to load measurements. Computer 362 can store calibration data that can be used to curve fit and compensate for non-linear output of a sensor over a range of operation. Furthermore, the individual sensor measurement can be combined to produce other measurement data by computer 362. In keeping with the example of load measurement data, the individual load measurement data can be combined or assessed to determine a location where the load is applied to a surface to which the load sensors couple. The measurement data can be displayed on a display that supports a surgeon rapidly assimilating the measurement data. For example, the calculated measurement data on the location of applied load to a surface may have little or no meaning to a surgeon. Conversely, an image of the surface being loaded with a contact point displayed on the surface can be rapidly assimilated by the surgeon to determine if there is an issue with the contact point.

In one embodiment, the knee joint system transmits and receives information wirelessly. Wireless operation reduces clutter within the surgical area, wired distortion of, or limitations on, measurements caused by the potential for physical interference by, or limitations imposed by, cables connecting a device with an internal power with data collection, storage, or display equipment in an operating room environment. Electronic circuitry 292 includes wireless communication circuitry 320. In one embodiment, wireless communication circuitry 320 is configured for short range telemetry and battery operation. Typically, medical device 250, and computer 362 are located in an operating room such that the transmission of measurement to computer 362 is less than 10 meters. As illustrated, the exemplary communications system comprises wireless communication circuitry 320 of medical device 250 and receiving system wireless communication circuitry 322 of computer 362. Wireless communications circuitry 320 comprises, but is not limited to, the antenna 360, a matching network 316, the telemetry transceiver 314, a CRC circuit 312, a data packetizer 310, and a data input 308. Wireless communication circuitry 320 can include more or less than the number of components shown and are not limited to those shown or the order of the components.

Similarly, computer 362 includes wireless communication circuitry 322. Wireless communication circuitry 322 comprises an antenna 324, a matching network 326, a telemetry transceiver 328, a CRC circuit 330, and a data packetizer 332. Notably, other interface systems can be directly coupled to the data packetizer 332 for processing and rendering sensor data. In general, electronic circuitry 292 couples to sensors 302 and is configured to transmit quantitative measurement data to computer 362 in real-time to process, display, analyze, and provide feedback. Medical device 250 includes a plurality of full bridge Poisson gauges configured to measure loads applied to surface module 254 or surface module 258. Medical device 250 further includes an inertial measurement unit comprising one or more inertial sensors and other parameter measurement sensors as listed herein above. The measurement data from the plurality of load sensors and the inertial sensors is transmitted to computer 362. Computer 362 can calculate a load magnitude applied to surface module 254 or surface module 258 from the plurality of load sensors. In the example, three load sensors at predetermined positions are used to measure a position of applied load and a load magnitude at the position of applied load. In one embodiment, computer 362 calculates a position of applied load (contact point) to surface module 254 or surface module 258 of medical device 250. Medical device 250 can further use measurement data from position measurement system 342 to monitor position and movement of medical device 250 or the musculoskeletal system. The position or tracking data from position measurement system 342 is also sent to computer 362. The results can also be displayed on display 364 of computer 362. In one embodiment, measurement data from position measurement system 342 can be used to measure range of motion, alignment, and impingement. In one embodiment, the transmission of the measurement data from different sensors or components can be sent on different channels or the measurement data can be sent at different times on the same channel.

As mentioned previously, wireless communication circuitry comprises data input 308, data packetizer 310, CRC circuit 312 telemetry transmitter 314, matching network 316, and antenna 360. In general, measurement data from sensors 302 is provided to data input 308 of wireless communication circuitry 320. In one embodiment, the measurement data from sensors 302 can come directly from interface circuitry 306, from memory 350 or from a combination of paths to data input 308. In one embodiment, measurement data can be stored in memory 350 prior to being provided to data input 308. Data packetizer 310 assembles the measurement data into packets and includes sensor information received or processed by memory 350. Memory 350 can comprise specific modules for efficiently performing core signal processing functions of the medical device 250. Memory 350 provides the further benefit of reducing the form factor to meet dimensional requirements for integration into medical device 250.

In general, measurement data from medical device 250 is encrypted. In one embodiment, the output of data packetizer 310 couples to the input of CRC circuit 312. CRC circuit 312 applies error code detection on the packet data. The cyclic redundancy check is based on an algorithm that computes a checksum for a data stream or packet of any length. These checksums can be used to detect interference or accidental alteration of data during transmission. Cyclic redundancy checks are especially good at detecting errors caused by electrical noise and therefore enable robust protection against improper processing of corrupted data in environments having high levels of electromagnetic activity. The output of CRC circuit 312 couples to the input of telemetry transceiver 314. The telemetry transceiver 314 then transmits the CRC encoded data packet through the matching network 316 by way of the antenna 360. Telemetry transceiver 314 can increase a carrier frequency in one or more steps and add the information or measurement data from medical device 250 to the carrier frequency. The matching network 316 provides an impedance match for achieving optimal communication power efficiency between telemetry transceiver 314 and antenna 360.

Antenna 360 can be integrated with components of the medical device 250 to provide the radio frequency transmission. The substrate for the antenna 360 and electrical connections with the electronic circuitry 292 can further include the matching network 316. In one embodiment, the antenna 360 and a portion of the matching network 316 can be a wire or formed in printed circuit board 270 that interconnects the components that comprise electronic circuitry 292. This level of integration of the antenna and electronics enables reductions in the size and cost of wireless equipment. Potential applications may include, but are not limited to any type musculoskeletal equipment or prosthetic components where a compact antenna can be used. This includes disposable modules or devices as well as reusable modules or devices and modules or devices for long-term use.

The process for receiving wireless communication circuitry 322 is the opposite of the sending process. Antenna 324 receives transmitted measurement data from wireless communication circuitry 320. Wireless communication circuitry 320 can transmit at low power such that receiving wireless communication circuitry 322 must be in proximity, for example within 10 meters to receive measurement data. Antenna 324 couples to matching network 326 that efficiently couples the measurement data to telemetry transceiver 328. The measurement data can be sent on a carrier signal that supports wireless transmission. The measurement data is stripped off from the carrier signal by telemetry transceiver 328. The measurement data is received by CRC circuit 330 from telemetry transceiver 328. CRC circuit 330 performs a cyclic redundancy check algorithm to verify that the measurement data has not been corrupted during transmission. The CRC circuit 330 provides the checked measurement data to data packetizer 332. Data packetizer 332 reassembles the measurement data where it is provided to USB interface 334. USB interface 334 provides the measurement data to computer 362 for further processing.

It should be noted that the measuring, transmitting, receiving, and processing of the measurement data can be performed in real-time for use by a surgeon to support installation of a prosthetic joint. In one embodiment, computer 362 displays at least a portion of medical device 250. In the example, surface module 254 or surface module 258 of medical device 250 is displayed on display 364 coupled to computer 362. Measurement data from sensors 302 and position measurement system 342 is used to calculate a load magnitude and a position of applied load on surface module 254 or surface module 258 of medical device 250. The location of each full bridge Poisson gauge is known relative to surface module 254 or surface module 258. The position of applied load can be calculated using the location information from each load sensor and the load magnitude at each location by computer 362 as disclosed in detail herein above. The position of applied load is also called contact point 382 on GUI 380 of display 364. Similarly, the load magnitude at contact point 382 can be calculated from three or more full bridge Poisson gauges and the locations of the three or more full bridge Poisson gauges relative to a surface of the surface module of medical device 250. In one embodiment, the minimum load, the maximum load, and the load at the current location are displayed on GUI 380 respectively in display boxes 380, 390, and 386. The amount of rotation or range of motion can also be indicated. These measurements are measured or calculated in real-time and displayed on display 364. Adjustments can be performed that affect alignment, loading, position of load, rotation, or other parameters and monitored in real-time on display 364. The adjustments can support optimization after the measured parameters are within specification to fine tune the prosthetic component installation with quantitative measurement data.

In general, a surgeon moves the knee joint through a range of motion to generate measurement data in a trialing of the knee joint. The measurement data from sensors 302 in medical device 150 is transmitted to computer 362. Computer 362 processes the information and displays the information in a manner where quantitative measurement data can be rapidly assimilated by the surgeon or surgical team. The measurement data can be displayed or it can be presented graphically or audibly. A picture of a portion of medical device 250 is displayed on display 364. In the example, a surface 384 is displayed on display 364 that corresponds to a surface of surface module 254 or surface module 258. In one embodiment, measurement data from sensors 302 at predetermined locations are used to determine contact point 382 on display 364. Display 364 can further add measurement data or graphics to disclose movement of contact point 384 on surface 384. In one embodiment, movement of contact point 384 will be non-linear. In one embodiment, display 364 may display a three dimensional type of animation to illustrate to a surgeon or surgical team a location of contact point 382 on surface 384. This allows the surgeon to understand loading or location of the loading at different leg positions over the range of motion. Alternatively, more than one view or different orientations of surface 384 can be provided on display 364 to better illustrate a location of contact point 382 on surface 384. A display box 386 discloses the load magnitude in real-time on GUI 380 as the knee joint is moved through the range of motion. In one embodiment, computer 362 or medical device 250 can include software having a force location and load magnitude algorithm that calculates contact point 382 and load magnitude as displayed in display box 386 from the measurement data received from medical device 250. In the example, the measurement data comprises information from three full bridge Poisson gauges measuring loading applied to the surface of surface module 254 or three full bridge Poisson gauges measuring loading applied to the surface of surface module 258. A reference sensor can also be incorporated in medical device 250 to support measurement accuracy.

Position measurement system 342 is configured to measure position or motion. In one embodiment, position measurement system 342 is configured to be housed in medical device 250. In one embodiment, position measurement system 342 is an inertial measurement unit (IMU). Computer 362 or medical device 250 can further have quaternion and range of motion algorithms to support measurement of movement and position. Calibration information can be accessed for the IMU or load sensors and used with the force location, load magnitude, and impingement measurements. In one embodiment, calibration information or calibration data corresponds to test measurements on medical device 250. In one embodiment, the calibration data can be stored on non-volatile memory such as EEPROM within medical device 250. As the knee joint is moved through a predetermined range of motion there will be a minimum load magnitude measured at a first location and a maximum load magnitude measured at a second location on surface 384 for a predetermined range of motion. The minimum load magnitude is indicated in display box 388 on GUI 380 that is continuously updated should a lower value occur. Similarly, the maximum load magnitude is indicated in display box 390 on GUI 380 that is continuously updated. In one embodiment, force vector data can be used to detect impingement. GUI 380 will notify the surgeon or surgical team when impingement is detected by audible, visual, or haptic means. In one embodiment, the IMU comprises one or more inertial sensors and is housed in medical device 250. The IMU can track position, motion, and can also be used in conjunction with the force vector data or alone to determine impingement. Impingement may not occur in a knee joint but can occur in other joints that are measured such as a shoulder joint or hip joint.

In the example, an exit button 492, a LOG button 494, a zero button 496, a reset button 392, and a ROM button 470 are provided on GUI 380. In one embodiment, exit button 492 toggles between coupling medical device 250 and decoupling medical device 250 from computer 362. In one embodiment, exit button 492 will indicate when medical device 250 is coupled to computer 362. In one embodiment, enabling LOG button 494 logs data for 10 seconds. In one embodiment, enabling zero button 496 zeroes load data offsets. In one embodiment, enabling reset button 392 resets display box 388 and display box 390 to the current load magnitude value. In one embodiment, enabling ROM button 370 initiates a range of motion test. ROM button 370 further initializes the IMU for the range of motion test. Battery indicator 426 indicates an amount of power left in the power source. In the example, the power source comprises one or more batteries. In one embodiment, battery indicator 426 indicates the percentage of power remaining in the one or more batteries of medical device 250. In one embodiment, indicator 426 can provide an estimation of an operating time of medical device 250 based on the average current drain from the batteries. GUI 380 further includes a tracking function that displays dynamic motion of contact point 382 through the full range of motion to evaluate joint kinetics. GUI 380 can also indicate or leave a location trace where loading exceeds a predetermined threshold.

Medical device 250 coupling to computer 362 is indicated on GUI 380. An indicator on GUI 380 shows the signal strength of the wireless connection to medical device 250. A signal strength is displayed on an indicator on display 364 that provides an indication of the connection and ability to transfer measurement data to computer 362. In one embodiment, the wireless connection is a Bluetooth low energy connection that opens a connection dialog between computer 362 and any Bluetooth devices. Computer 362 is used to select medical device 250 for connection and initiates the wireless connection. In one embodiment, calibration data and device information from medical device 250 is downloaded to computer 362. Medical device 250 couples to computer 362 and begins to stream measurement data. In one embodiment, GUI 380 zeroes any load data and then begins showing a measured load magnitude at contact point 382 in display box 386.

Impingement occurs when a prosthetic joint impinges on bone or soft tissue. Impingement may also occur in the soft tissue around a prosthetic joint. Soft tissue impingement is often called acromial impingement. Impingement information can be displayed on GUI 380. In one embodiment, a rim of the surface on display 364 is used to show if impingement occurs and approximately where the impingement occurs. A portion of the rim will be highlighted by a color change or a gray scale change on the portion of the rim in proximity to where the impingement occurs. In one embodiment, the portion of the rim in proximity to the impingement will turn red when impingement is detected.

Figure 12:
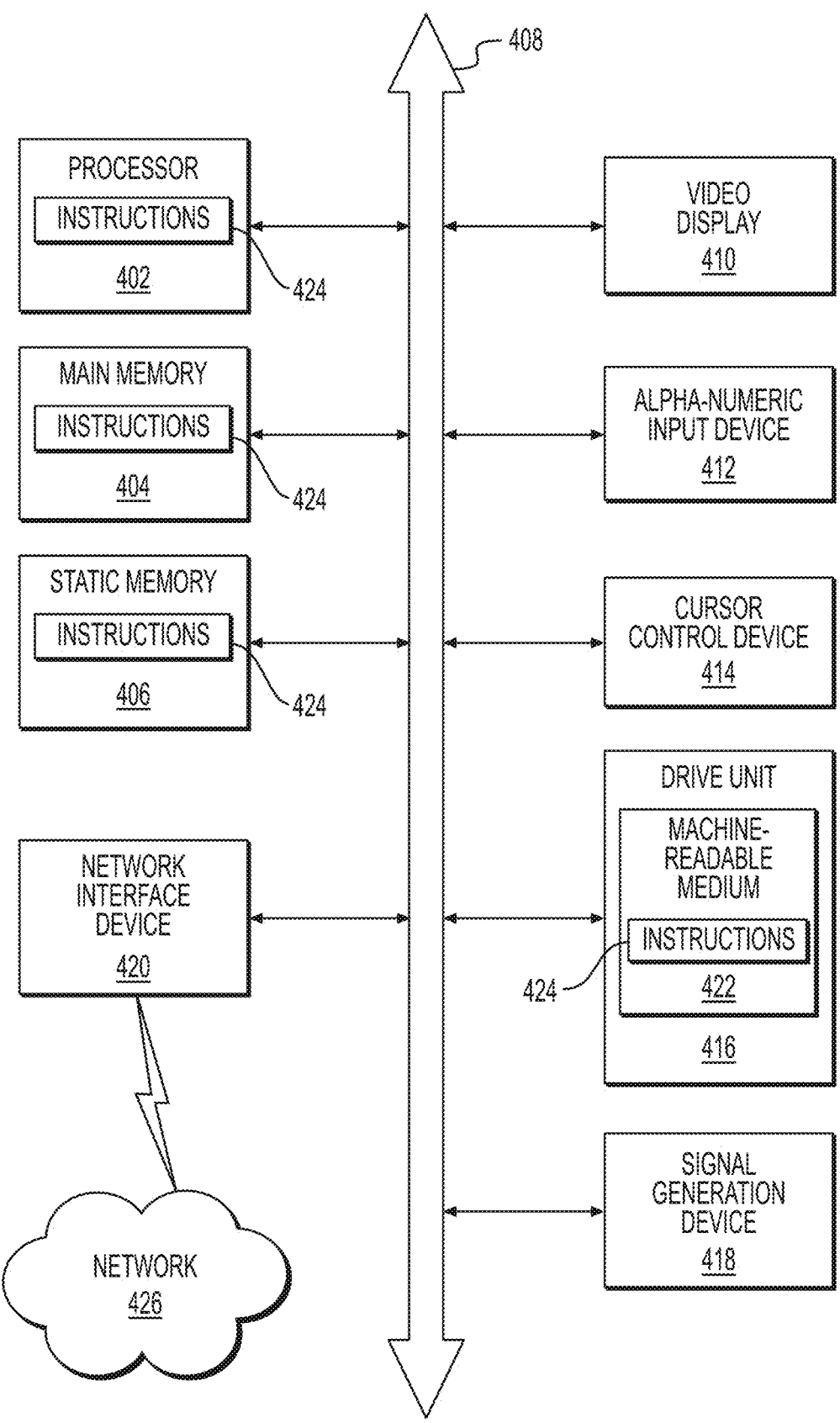
FIG. 12 is a block diagram of a system or a computer in accordance with an example embodiment.

FIG. 12 is a block diagram of a system or a computer in accordance with an example embodiment. The exemplary diagrammatic representation of a machine, device, system, or computer in the form of a system within which a set of instructions, when executed, may cause the machine to perform any one or more of the methodologies discussed above. In some embodiments, the machine operates as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a laptop computer, a desktop computer, a control system, logic circuitry, a sensor system, an ASIC, an integrated circuit, a network router, switch or bridge, or any machine capable of executing a set of instructions (sequential or otherwise) that specify actions to be taken by that machine. It will be understood that a device of the present disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methodologies discussed herein.

The system may include a processor 402 (e.g., a central processing unit (CPU), a graphics processing unit (GPU, or both), a main memory 404 and a static memory 406, which communicate with each other via a bus 408. The system may further include a video display unit 410 (e.g., a liquid crystal display (LCD), a flat panel display, a solid state display, or a cathode ray tube display (CRT)). The system may include an input device 412 (e.g., a keyboard), a cursor control device 414 (e.g., a mouse), a disk drive unit 416, a signal generation device 418 (e.g., a speaker or remote control) and a network interface device 420.

The drive unit 416 can be other types of memory such as flash memory and may include a machine-readable medium 422 on which is stored one or more sets of instructions 424 (e.g., software) embodying any one or more of the methodologies or functions described herein, including those methods illustrated above. Instructions 424 may also reside, completely or at least partially, within the main memory 404, the static memory 406, and/or within the processor 402 during execution thereof by the system. Main memory 404 and the processor 402 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine readable medium containing instructions 424, or that which receives and executes instructions 424 from a propagated signal so that a device connected to a network environment 420 can send or receive voice, video or data, and to communicate over the network 426 using the instructions 424. The instructions 424 may further be transmitted or received over the network 426 via the network interface device 420.

While the machine-readable medium 422 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; and carrier wave signals such as a signal embodying computer instructions in a transmission medium; and/or a digital file attachment to e-mail or other self-contained information archive or set of archives is considered a distribution medium equivalent to a tangible storage medium. Accordingly, the disclosure is considered to include any one or more of a machine-readable medium or a distribution medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same functions are considered equivalents.

Figure 13:
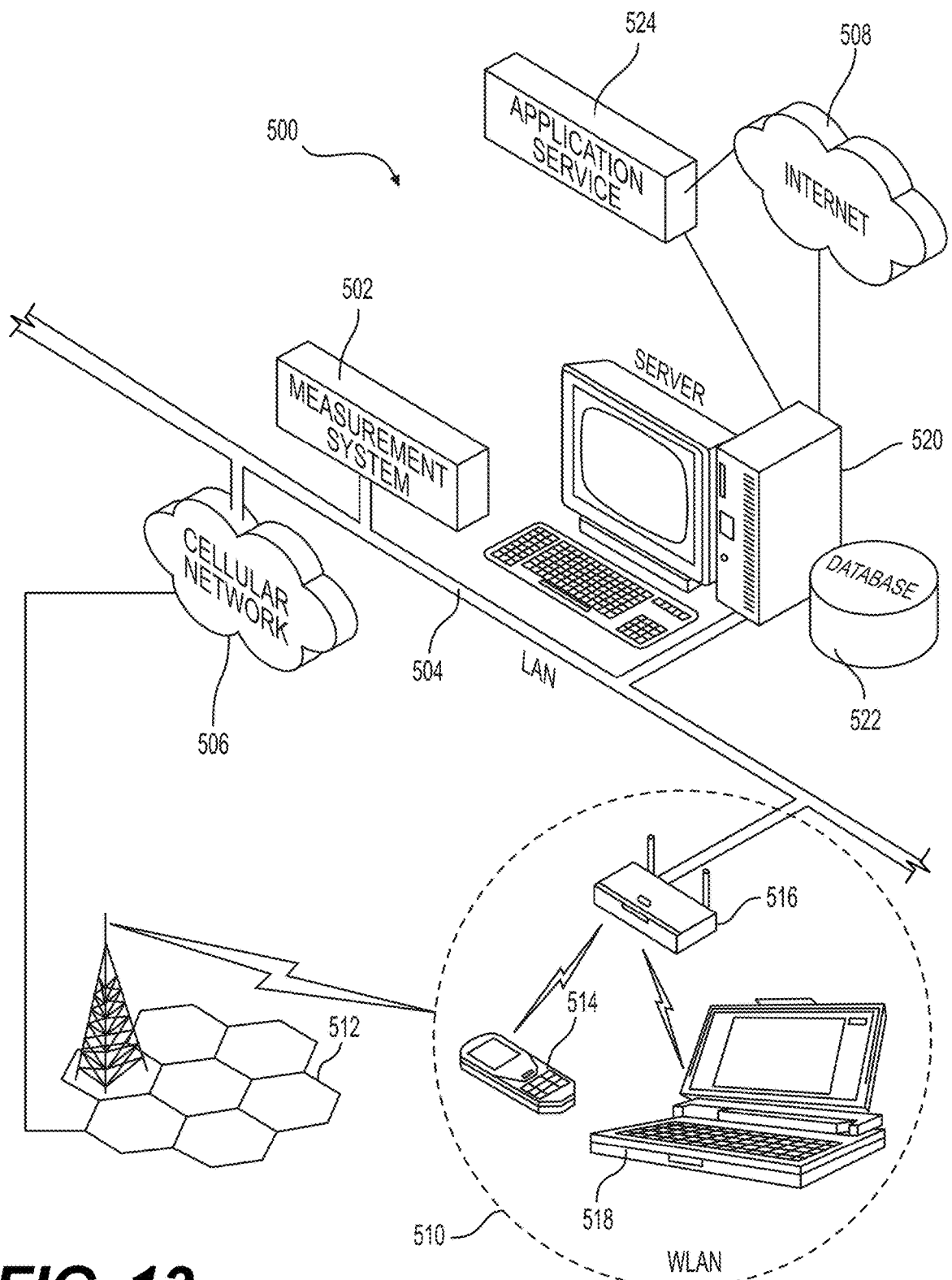
FIG. 13 is an illustration of a communication network for measurement and reporting in accordance with an exemplary embodiment.

FIG. 13 is an illustration of a communication network 500 for measurement and reporting in accordance with an exemplary embodiment. Briefly, the communication network 500 expands broad data connectivity to other devices or services. As illustrated, the measurement system 502 can be communicatively coupled to the communications network 500 and any associated systems or services.

As one example, measurement system 502 can share its parameters of interest (e.g., angles, load, balance, distance, alignment, displacement, movement, rotation, and acceleration) with remote services or providers, for instance, to analyze or report on surgical status or outcome. This data can be shared for example with a service provider to monitor progress or with plan administrators for surgical monitoring purposes or efficacy studies. The communication network 500 can further be tied to an Electronic Medical Records (EMR) system to implement health information technology practices. In other embodiments, the communication network 500 can be communicatively coupled to HIS Hospital Information System, HIT Hospital Information Technology and HIM Hospital Information Management, EHR Electronic Health Record, CPOE Computerized Physician Order Entry, and CDSS Computerized Decision Support Systems. This provides the ability of different information technology systems and software applications to communicate, to exchange data accurately, effectively, and consistently, and to use the exchanged data.

The communications network 500 can provide wired or wireless connectivity over a Local Area Network (LAN) 504, a Wireless Local Area Network (WLAN) 510, a Cellular Network 506, and/or other radio frequency (RF) system. The LAN 504 and WLAN 510 can be communicatively coupled to the Internet 508, for example, through a central office. The central office can house common network switching equipment for distributing telecommunication services. Telecommunication services can include traditional POTS (Plain Old Telephone Service) and broadband services such as cable, HDTV, DSL, VoIP (Voice over Internet Protocol), IPTV (Internet Protocol Television), Internet services, and so on.

The communication network 500 can utilize common computing and communications technologies to support circuit-switched and/or packet-switched communications. Each of the standards for Internet 508 and other packet switched network transmission (e.g., TCP/IP, UDP/IP, HTML, HTTP, RTP, MMS, or SMS) represent examples of the state of the art. Such standards are periodically superseded by faster or more efficient equivalents having essentially the same functions. Accordingly, replacement standards and protocols having the same functions are considered equivalent.

The cellular network 506 can support voice and data services over a number of access technologies such as GSM-GPRS, EDGE, CDMA, UMTS, WiMAX, 2G, 3G, 4G, 5G, WAP, software defined radio (SDR), and other known technologies. The cellular network 506 can be coupled to base receiver 512 under a frequency-reuse plan for communicating with mobile devices 514.

The base receiver 512, in turn, can connect the mobile device 514 to the Internet 508 over a packet switched link. The internet 508 can support application services and service layers for distributing data from the measurement system 502 to the mobile device 514. Mobile device 514 can also connect to other communication devices through the Internet 508 using a wireless communication channel. The mobile device 514 can also connect to the Internet 508 over the WLAN 510. Wireless Local Access Networks (WLANs) provide wireless access within a local geographical area. WLANs are typically composed of a cluster of Access Points (APs) 516 also known as base stations. The measurement system 502 can communicate with other WLAN stations such as laptop 518 within the base station area. In typical WLAN implementations, the physical layer uses a variety of technologies such as 802.11b, 802.11g, 802.11n, 802.11ac, or WLAN technologies. The physical layer may use infrared, frequency hopping spread spectrum in the 2.4 GHz Band, direct sequence spread spectrum in the 2.4 GHz Band, or other access technologies, for example, in the 5.8 GHz ISM band or higher ISM bands (e.g., 24 GHZ, etcetera).

By way of the communication network 500, the measurement system 502 can establish connections with a remote server 520 on the network and with other mobile devices for exchanging data. The remote server 520 can have access to a database 522 that is stored locally or remotely and which can contain application specific data. The remote server 420 can also host application services directly, or over the internet 508.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the claims. While the subject matter of the invention is described with specific examples of embodiments, the foregoing drawings and descriptions thereof depict only typical embodiments of the subject matter and are not therefore to be considered to be limiting of its scope, it is evident that many alternatives and variations will be apparent to those skilled in the art. Thus, the description of the invention is merely descriptive in nature and, thus, variations that do not depart from the gist of the invention are intended to be within the scope of the embodiments of the present invention. Such variations are not to be regarded as a departure from the spirit and scope of the present invention.

While the present invention has been described with reference to embodiments, it is to be understood that the invention is not limited to the disclosed embodiments. The scope of the following claims is to be accorded the broadest interpretation so as to encompass all modifications, equivalent structures and functions. For example, if words such as "orthogonal", "perpendicular" are used the intended meaning is "substantially orthogonal" and "substantially perpendicular" respectively. Additionally although specific numbers may be quoted in the claims, it is intended that a number close to the one stated is also within the intended scope, i.e. any stated number (e.g., 90 degrees) should be interpreted to be "about" the value of the stated number (e.g., about 90 degrees).

As the claims hereinafter reflect, inventive aspects may lie in less than all features of a single foregoing disclosed embodiment. Thus, the hereinafter expressed claims are hereby expressly incorporated into this Detailed Description of the Drawings, with each claim standing on its own as a separate embodiment of an invention. Furthermore, while some embodiments described herein include some but not other features included in other embodiments, combinations of features of different embodiments are meant to be within the scope of the invention, and form different embodiments, as would be understood by those skilled in the art.

What is claimed is:

1. A medical sensor comprising:
   a substrate configured to flex in a first direction, wherein the substrate has a center and a centerline, and wherein the substrate is configured to have a region of maximum strain;
   a dielectric layer overlying the substrate;
   a first strain gauge overlying the dielectric layer;
   a second strain gauge overlying the dielectric layer;
   a third strain gauge overlying the dielectric layer,
      wherein the second strain gauge and the third strain gauge are positioned on the substrate outside the region of maximum strain, and
      wherein the second strain gauge and the third strain gauge are configured to measure strain in the first direction; and
   a fourth strain gauge overlying the dielectric layer,
      wherein the first strain gauge and the fourth strain gauge are spaced apart from the centerline,
      wherein the first strain gauge and the fourth strain gauge are configured to be active when a first force causes the substrate to flex in a second direction, and
      wherein the second strain gauge and the third strain gauge are configured to be inactive when the first force causes the substrate to flex in the second direction.

2. The medical sensor of claim 1, wherein the first strain gauge, the second strain gauge, the third strain gauge, and the fourth strain gauge form a full bridge Poisson gauge.

3. The medical sensor of claim 2, wherein the second strain gauge and the third strain gauge are configured to be active when a second force causes the substrate to flex in the first direction.

4. The medical sensor of claim 2, wherein the first strain gauge and the fourth strain gauge are configured to be active when a second force causes the substrate to flex in the first direction.

5. The medical sensor of claim 2, further including:
   an interconnect formed overlying the dielectric layer; and
   a plurality of pads formed overlying the dielectric layer,
      wherein the interconnect is configured to couple the first strain gauge, the second strain gauge, the third strain gauge, and the fourth strain gauge into the full bridge Poisson gauge, and
      wherein the interconnect is configured to couple the full bridge Poisson gauge to the plurality of pads.

6. The medical sensor of claim 5, wherein the plurality of pads are surface mount technology (SMT) pads and wherein the medical sensor is configured to be a surface mount device configured to be placed and coupled to a printed circuit board within a medical device.

7. The medical sensor of claim 6, wherein the first strain gauge, the second strain gauge, the third strain gauge, and the fourth strain gauge are formed by sputtering metal on the dielectric layer, and wherein the sputtered metal is patterned to form the first strain gauge, the second strain gauge, the third strain gauge, and the fourth strain gauge.

8. The medical sensor of claim 1, wherein the dielectric layer comprises polyamide.

9. The medical sensor of claim 1, wherein the substrate comprises 17-7 heat treated stainless steel.

10. The medical sensor of claim 9, wherein at least one dimension of the substrate is 0.80 millimeters or less.

11. A medical sensor comprising:
    a substrate configured to flex in a first direction, wherein the substrate has a center and a centerline, and wherein the substrate is configured to have a region of maximum strain;
    a dielectric layer overlying the substrate;
    a first strain gauge overlying the dielectric layer;
    a second strain gauge overlying the dielectric layer;
    a third strain gauge overlying the dielectric layer, wherein the second strain gauge and the third strain gauge are positioned along a first line parallel to the centerline and traversing the region of maximum strain, and wherein the second strain gauge and the third strain gauge are configured to measure strain in the first direction;

a fourth strain gauge overlying the dielectric layer,
wherein the first strain gauge and the fourth strain gauge are positioned along a second line perpendicular to the centerline, and wherein the first strain gauge and the fourth strain gauge are configured to be inactive when a first force causes the substrate to flex in the first direction; and an interconnect formed overlying the dielectric layer,
wherein the interconnect is configured to couple the first strain gauge, the second strain gauge, the third strain gauge, and the fourth strain gauge into a full bridge Poisson gauge.

12. The medical sensor of claim 11, wherein the medical sensor is a prosthetic component.

13. The medical sensor of claim 12, wherein loading applied to the prosthetic component is configured to be applied at least to the center of the substrate.

14. The medical sensor of claim 12, wherein the medical sensor has a first support configured to couple to a first end of the substrate, wherein the medical device has a second support configured to couple to a second end of the substrate, and wherein the first strain gauge and the fourth strain gauge are positioned on the substrate outside the region of maximum strain.

15. The medical sensor of claim 11, wherein the second strain gauge and the third strain gauge are configured to be active for measuring strain applied to the medical sensor.

16. The medical sensor of claim 11, wherein the dielectric layer comprises polyamide.

17. The medical sensor of claim 11, wherein the substrate comprises 17-7 heat treated stainless steel and wherein at least one dimension of the substrate is 0.80 millimeters or less.

18. A medical sensor comprising:
a substrate configured to flex in a first direction, wherein the substrate has a center and a centerline;
a dielectric layer formed overlying the substrate;
a full bridge Poisson gauge,
wherein the full bridge Poisson gauge includes a first strain gauge, a second strain gauge, a third strain gauge, and a fourth strain gauge overlying the dielectric layer, wherein the second strain gauge and the third strain gauge are positioned along a first line parallel to the centerline and spaced apart from the center, wherein the second strain gauge and the third strain gauge are configured to measure strain in the first direction, wherein the first strain gauge and the fourth strain gauge are positioned along a second line perpendicular to the centerline and spaced apart from the center, wherein the first strain gauge and the fourth strain gauge are configured to be inactive when a first force causes the substrate to flex in the first direction, and wherein the medical sensor is configured to be coupled to a printed circuit board, wherein the substrate is configured to have a region of maximum strain, and wherein the region of maximum strain occurs at the centerline.

19. The medical sensor of claim 18,
wherein the second strain gauge and the third strain gauge are placed symmetrical about the center of the substrate, and
wherein the second strain gauge and the third strain gauge are placed on the centerline.

20. The medical sensor of claim 19, wherein the dielectric layer comprises polyamide, wherein the substrate comprises 17-7 heat treated stainless steel, and wherein at least one dimension of the substrate is 0.80 millimeters or less.

* * * * *